(12) United States Patent
Koch et al.

(10) Patent No.: US 11,535,672 B2
(45) Date of Patent: Dec. 27, 2022

(54) COMBINATION OF AN ANTI-CD16A ANTIBODY WITH A CYTOKINE

(71) Applicant: Affimed GmbH, Heidelberg (DE)

(72) Inventors: Joachim Koch, Heidelberg (DE); Martin Treder, Heidelberg (DE); Jens Pahl, Dossenheim (DE); Uwe Reusch, Maikammer (DE); Thorsten Ross, Edingen-Neckarhausen (DE); Erich Rajkovic, Schriessheim (DE); Adelheid Cerwenka, Heidelberg (DE)

(73) Assignee: AFFIMED GMBH, Heidelberg (DE)

( * ) Notice: Subject to any disclaimer, the term of this patent is extended or adjusted under 35 U.S.C. 154(b) by 155 days.

(21) Appl. No.: 16/521,470

(22) Filed: Jul. 24, 2019

(65) Prior Publication Data
US 2020/0010547 A1    Jan. 9, 2020

Related U.S. Application Data

(63) Continuation of application No. PCT/EP2018/054990, filed on Feb. 28, 2018.

(30) Foreign Application Priority Data

Feb. 28, 2017    (EP) .................... 17158563

(51) Int. Cl.
*A61K 39/395* (2006.01)
*A61K 38/20* (2006.01)
*C07K 16/28* (2006.01)
*C07K 14/54* (2006.01)
(Continued)

(52) U.S. Cl.
CPC ............ *C07K 16/283* (2013.01); *A61K 38/19* (2013.01); *A61K 38/204* (2013.01); *A61K 38/208* (2013.01); *A61K 38/2013* (2013.01); *A61K 38/2086* (2013.01); *A61K 39/39558* (2013.01); *C07K 14/5412* (2013.01); *C07K 14/5434* (2013.01); *C07K 14/5443* (2013.01); *C07K 14/55* (2013.01); *C07K 16/2878* (2013.01); *A61K 38/20* (2013.01); *C07K 14/54* (2013.01);
(Continued)

(58) Field of Classification Search
None
See application file for complete search history.

(56) References Cited

U.S. PATENT DOCUMENTS 9,284,375 B2 *  3/2016  Johnson .............. C07K 16/283

FOREIGN PATENT DOCUMENTS

WO    2016177846 A1    11/2016

OTHER PUBLICATIONS

Romee et al, Utilizing cytokines to function-enable human NK cells for the immunotherapy of cancer, Scientifica, vol. 2014: Article ID 205796, 18 pages, Jun. 25, 2014.*

(Continued)

*Primary Examiner* — Claire Kaufman
(74) *Attorney, Agent, or Firm* — Perkins Coie LLP; Viola Kung

(57) ABSTRACT

The invention relates to an anti-CD16A antigen binding protein for use in NK cell-based immunotherapy, wherein the anti-CD16A antigen binding protein is to be administered intermittently and in combination with a cytokine. In certain embodiments the antigen binding protein is a tetravalent and bispecific CD30/CD16A tandem diabody.

28 Claims, 19 Drawing Sheets
Specification includes a Sequence Listing.

(51) Int. Cl.
    C07K 14/55         (2006.01)
    A61K 38/19         (2006.01)
(52) U.S. Cl.
    CPC .... C07K 2317/34 (2013.01); C07K 2317/626
                  (2013.01); C07K 2317/732 (2013.01)

(56) References Cited

OTHER PUBLICATIONS

Felices et al., Generation of BiKEs and TriKEs to improve NK cell-mediated targeting of tumor cells, Meth. Mol. Biol. 1441:333-346, Jan. 2016.*

Bleumer et al., The clinical trial with chimeric monoclonal antibody WX-G250 and low dose interleukin-2 pulisng scheme for advanced renal cell carcinoma, J. Urol.175:57-62, Jan. 2006.*

Hartmann et al., Anti-CD16/CD30 bispecific antibody treatment for Hodgkin's disease:role of infusion schedule and costimulation with cytokines, Clin. Canc. Res. 7:1873-181, Jul. 2001.*

Bleumer et al., A phase II trial of chimeric monoclonal antibody G250 for advanced renal cell carcinoma patients, Brit. J. Canc. 90: 985-990, 2004.*

Reusch et al., A novel tetravalent bispecific TandAb (CD30/CD16A) efficiently recruits NK cells for the lysis ofCD30+ tumor cells, mAbs, 6(3):727-738, 2014.*

Wu et al.,AFM13: a first-in-class tetravalent bispecific anti-CD30/CD16A antibody for NK cell-mediated immunotherapy, J. Hematol., Oncol. 8:96, 4 pages, Aug. 1, 2015.*

Yan et al., Construction of a synthetic phage-displayed Nanobody library with CDR3 regions randomized by trinucleotide cassettes for diagonistic applications, J. Transl. Med. 12:343, 2014.*

Bessard et al., High antitumor activity of RLI, an interleukin-15 (IL-15)-IL-15 receptor α fusion protein, in metastatic melanoma and colorectal cancer, Mol. Canc. Ther. 8(9):2736-2745, 2009.*

Hank et al., Distinct clinical and laboratory activity of two recombinant interleukin-2 preparations, Clin. Canc. Res.5:281-289, Feb. 1999.*

BLINCYTO Prescribing Information, Retrieved online: URL<<https://www.accessdata.fda.gov/drugsatfda_docs/label/2014/125557lbl.pdf>. [Retrieved on Oct. 12, 2022], Dec. 2014.*

Jens Pahl, et al., "AFM13 Is the Most Advanced Bispecific NK-Cell Engaging Antibody in Clinical Development Substantially Enhancing NK-Cell Effector Function and Proliferation", Biosciences Information Service, Dec. 2, 2016.

Jens Pahl, et al., "NK cell Activation by the bispecific CD30/CD16A TandAb AFM13 substantially enhances NK cell effector functions and proliferation" Sep. 29, 2016, Retrieved from Internet:URL:https://www.nk2016.it/pdf/nk-cell-activation-and-memory/Pahl%20Jens.pdf [retrieved on Jun. 30, 2017].

Jens HW Pahl, et al., "CD16A activation of NK cells promotes NK cell proliferation and memory-like cytotoxicity against cancer cells", Cancer Immunology Research, Mar. 7, 2018.

Jens Pahl, et al., "Abstract 2997: The tetravalent bispecific antibody AFM13 engages and primes innate immune cells for anti-cancer immunity", AACR Annual Meeting Cancer Research, vol. 77, No. 13 Suppl, Apr. 2017.

International Search Report dated Jul. 11, 2018 cited in PCT/EP2018/054990.

Jens Pahl, et al., "AFM13 Is the Most Advanced Bispecific NK-Cell Engaging Antibody in Clinical Development Substantially Enhancing NK-Cell Effector Function and Proliferation", Poster Presentation, Dec. 5, 2016, Blood 128 (22): 1764, Dec. 2016.

* cited by examiner

A

B

SEQUENCE LISTING

```
<160> NUMBER OF SEQ ID NOS: 10

<210> SEQ ID NO 1
<211> LENGTH: 8
<212> TYPE: PRT
<213> ORGANISM: artificial sequence
<220> FEATURE:
<223> OTHER INFORMATION: CDR

<400> SEQUENCE: 1

Gly Tyr Thr Phe Thr Ser Tyr Tyr
1               5

<210> SEQ ID NO 2
<211> LENGTH: 8
<212> TYPE: PRT
<213> ORGANISM: artificial sequence
<220> FEATURE:
<223> OTHER INFORMATION: CDR

<400> SEQUENCE: 2

Ile Glu Pro Met Tyr Gly Ser Thr
1               5

<210> SEQ ID NO 3
<211> LENGTH: 13
<212> TYPE: PRT
<213> ORGANISM: artificial sequence
<220> FEATURE:
```

-continued

<223> OTHER INFORMATION: CDR

<400> SEQUENCE: 3

Ala Arg Gly Ser Ala Tyr Tyr Tyr Asp Phe Ala Asp Tyr
1               5                   10

<210> SEQ ID NO 4
<211> LENGTH: 6
<212> TYPE: PRT
<213> ORGANISM: artificial sequence
<220> FEATURE:
<223> OTHER INFORMATION: CDR

<400> SEQUENCE: 4

Asn Ile Gly Ser Lys Asn
1               5

<210> SEQ ID NO 5
<211> LENGTH: 4
<212> TYPE: PRT
<213> ORGANISM: artificial sequence
<220> FEATURE:
<223> OTHER INFORMATION: cdr

<400> SEQUENCE: 5

Gln Asp Asn Lys
1

<210> SEQ ID NO 6
<211> LENGTH: 9
<212> TYPE: PRT
<213> ORGANISM: artificial sequence
<220> FEATURE:
<223> OTHER INFORMATION: CDR

<400> SEQUENCE: 6

Gln Val Trp Asp Asn Tyr Ser Val Leu
1               5

<210> SEQ ID NO 7
<211> LENGTH: 8
<212> TYPE: PRT
<213> ORGANISM: artificial sequence
<220> FEATURE:
<223> OTHER INFORMATION: CDR

<400> SEQUENCE: 7

Ile Asn Pro Ser Gly Gly Ser Thr
1               5

<210> SEQ ID NO 8
<211> LENGTH: 120
<212> TYPE: PRT
<213> ORGANISM: artificial sequence
<220> FEATURE:
<223> OTHER INFORMATION: vh

<400> SEQUENCE: 8

Gln Val Gln Leu Val Gln Ser Gly Ala Glu Val Lys Lys Pro Gly Glu
1               5                   10                  15

Ser Leu Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ala Ile Glu Pro Met Tyr Gly Ser Thr Ser Tyr Ala Gln Lys Phe

```
                 50                  55                  60
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                     85                  90                  95

Ala Arg Gly Ser Ala Tyr Tyr Asp Phe Ala Asp Tyr Trp Gly Gln
                100                 105                 110

Gly Thr Leu Val Thr Val Ser Ser
            115                 120

<210> SEQ ID NO 9
<211> LENGTH: 106
<212> TYPE: PRT
<213> ORGANISM: artificial sequence
<220> FEATURE:
<223> OTHER INFORMATION: vl

<400> SEQUENCE: 9

Ser Tyr Val Leu Thr Gln Pro Ser Ser Val Ser Val Ala Pro Gly Gln
 1               5                  10                  15

Thr Ala Thr Ile Ser Cys Gly Gly His Asn Ile Gly Ser Lys Asn Val
                20                  25                  30

His Trp Tyr Gln Gln Arg Pro Gly Gln Ser Pro Val Leu Val Ile Tyr
             35                  40                  45

Gln Asp Asn Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Met
 65                  70                  75                  80

Asp Glu Ala Asp Tyr Tyr Cys Gln Val Trp Asp Asn Tyr Ser Val Leu
                 85                  90                  95

Phe Gly Gly Gly Thr Lys Leu Thr Val Leu
                100                 105

<210> SEQ ID NO 10
<211> LENGTH: 120
<212> TYPE: PRT
<213> ORGANISM: artificial sequence
<220> FEATURE:
<223> OTHER INFORMATION: vh

<400> SEQUENCE: 10

Gln Val Gln Leu Val Gln Ser Gly Ala Glu Val Lys Lys Pro Gly Glu
 1               5                  10                  15

Ser Leu Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Ser Ala Tyr Tyr Asp Phe Ala Asp Tyr Trp Gly Gln
                100                 105                 110

Gly Thr Leu Val Thr Val Ser Ser
            115                 120
```

COMBINATION OF AN ANTI-CD16A ANTIBODY WITH A CYTOKINE

This application is a continuation of PCT/EP2018/054990, filed Feb. 28, 2018; which claims the priority of EP 17158563.1, filed Feb. 28, 2017. The contents of the above-identified applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Jul. 24, 2019, and a size of 4.5 kilobytes. The Sequence Listing filed via EFS-Web is part of the specification and is hereby incorporated in its entirety by reference herein.

FIELD OF THE INVENTION

The present invention relates to a CD16A engaging antigen binding protein intermittently administered with a cytokine for NK cell-based immunotherapy. In particular embodiments, the present invention relates to a bispecific and tetravalent tandem diabody with CD16A antigen binding sites for engaging NK cells for use in the treatment of cancer or (virus) infections, wherein the tandem diabody is intermittently administered in combination with a cytokine. Examples are CD16A engaging tandem diabodies such as CD30/CD16A tandem diabody AFM13, the EGFR/CD16A tandem diabody AFM24, and the BCMA/CD16A tandem diabody AFM26.

BACKGROUND OF THE INVENTION

WO2006/125668 describes an antigen binding protein, i.e. CD30/CD16A bispecific tandem diabody, and its use for NK cell-based immunotherapy.

WO2016/177846 describes a combination of a CD30/CD16A bispecific tandem diabody and a PD-1 antagonist for its use in the treatment of Hodgkin lymphoma.

Natural Killer (NK) cells are cytotoxic, IFN-γ-producing innate lymphocytes that are considered to constitute the first line of defense against virus-infected cells and cancer cells (Cerwenka and Lanier, 2001; Spits, et al., 2013).

In contrast to CD8+ T cells, NK cells discriminate abnormal cells through a defined set of germline-encoded receptors such as the inhibitory KIR and NKG2A receptors and the activating NKG2D, DNAM-1 and NCR receptors (Koch et al, 2013; Pahl and Cerwenka, 2017). NK cells respond to cells that display reduced levels or an incompatible repertoire of inhibitory MHC class I molecules, enabling recognition of certain cancer cells which may have evaded CD8+ T cell responses. Low expression of inhibitory ligands in combination with high levels of activating ligands on target cells results in NK cell activation and the release of perforin and granzyme B, mediating target cell death (Gasser and Raulet, 2006; Moretta, et al., 2006). Besides, NK cell activation is triggered by cytokines such as IL-2 or IL-15 that augment NK cell responsiveness to target cells (Koehl et al, 2016).

In addition to their direct anti-tumor activity, NK cells contribute to the induction of adaptive anti-cancer responses and can perform immunoregulatory functions (Schuster, et al., 2016). Accumulating evidence supports the concept that NK cell subsets can encompass broad phenotypic and functional diversity (Roelle and Brodin, 2016; Tesi, et al., 2016). Moreover, NK cells can acquire properties of adaptive immunity and immunological memory such as specific subset expansion and antigen-specific responses (Sun, et al., 2014). In this context, pre-activation of NK cells by IL-12/15/18 has been shown to amplify and prolong NK cell responsiveness to tumor cells and cytokines which was associated with epigenetic remodeling of the IFN-γ locus (Cerwenka and Lanier, 2016; Luetke-Eversloh, et al., 2014; Ni, et al., 2016; Romee et al., 2016).

While NK cells, by definition, do not require prior sensitization, freshly-isolated (i.e. 'naïve') human NK cells without further activation are reactive to only a limited number of tumor cells such as the prototypical target cell line K562 (Vivier, 2011). In particular, NK cells from cancer patients show low reactivity towards autologous tumor cells unless ex vivo activated with cytokines (Parkhurst, et al., 2011, Reiners, et al., 2013). This may reflect inadequate tumor cell recognition, inhibitory effects of the immunosuppressive cancer microenvironment and the continuous modulation of NK cell responsiveness in vivo.

Tumor-reactive therapeutic antibodies can significantly improve the cytotoxicity of naïve NK cells towards tumor cells even in the presence of self-MHC class I (Harris, 2004; Pahl, et al., 2012; Parkhurst, et al., 2011; Reiners, et al., 2013). This antibody-mediated cellular cytotoxicity (ADCC) is mediated by the recognition of the human Fc portion of humanized and chimeric IgG1 antibodies by the ITAM-coupled NK cell-activating receptor CD16A (FcγRIIIA) (de Landazuri, et al., 1979; Lanier, et al., 1988; Vivier, et al., 1991). A role for NK cells and ADCC in the clinical response of therapeutic antibodies has been inferred from the observation that patients carrying high affinity CD16A allotypes (158V vs. 158F gene polymorphisms) have a more favorable prognosis (Bibeau, et al., 2009; Dall'Ozzo, et al., 2004; Musolino, et al., 2008).

However, multiple myeloma patients have elevated serum IgG levels compared to other cancer patients or healthy individuals and the disparity in CD16A affinities in myeloma patients as well as the potential competition for CD16A binding of human IgG at such pathophysiological serum concentrations with conventional therapeutic antibodies may hamper the full potential of ADCC and NK cells in vivo (Li, et al., 2016). To improve CD16A engagement, antibody formats have been developed that bind CD16A in an Fc-independent manner with high affinity (Rothe, et al., 2015; Wiernik, et al., 2013). AFM13 is a tetravalent bispecific CD30/CD16A tandem diabody (TandAb®) with bivalent binding to both CD30 and CD16A with high affinity and specificity (Reusch, et al., 2014). AFM13 is being tested in Phase 2 monotherapy and in combination with pembrolizumab in Phase 1b clinical trials in patients with CD30+ classical and non-classical Hodgkin lymphomas (WO2016/177846).

SUMMARY OF THE INVENTION

Although CD16A is a potent activating receptor on human NK cells, mediating NK cell cytotoxicity towards antibody-opsonized cancer cells, it is desired to further increase the efficiency and potency for activating the cytotoxicity of NK cells through CD16A engagement by an antigen binding protein.

The present inventors have found that CD16A engagement by a multispecific antibody such as the bispecific CD30/CD16A tandem diabody (AFM13) alters the phenotype and function of primary NK cells. After initially improving NK cell functionality, anti-CD16A antigen binding protein exposure (via tandem diabody) leads to a transient selective reduction in cytotoxic potency. However, this impaired NK cytotoxicity can be reverted by cytokine stimulation. In the examples it is shown that after culturing of the NK cells in the presence of IL-2 for a period without antigen binding protein exposure, these CD16A-experienced NK cells demonstrate more vigorous cytotoxicity and IFN-γ production when re-stimulated with cytokines or otherwise resistant tumor cells, indicative of a memory-like functionality.

Hence, the invention presented herein reveals a yet unappreciated role for CD16A triggering in priming and amplifying NK cell responses to cytokines and to subsequent re-stimulation by tumor cells. The present invention provides an intermittent administration regimen of an anti-CD16A antigen binding protein, e.g. the CD30/CD16A tandem diabody (AFM13), the EGFR/CD16A tandem diabody AFM24 or the BCMA/CD16A tandem diabody AFM26, either one in combination with a treatment by NK cell-activating cytokines for a period without exposure to the anti-CD16A antigen binding protein that improves NK cell responses.

The invention reveals a novel additional role for CD16A in priming and amplifying NK cell responses to cytokines and to subsequent re-stimulation by tumor cells. This means that, stimulation with the CD30/CD16A tandem diabody in the examples may not only enable killing of non-opsonized CD30⁺ tumor cells but even of CD30⁺ tumor cells, which are not directly targeted by the CD30/CD16A tandem diabody. These findings warrant an intermittent regimen of the anti-CD16A antigen binding protein in combination with a cytokine. This intermittent and combinatorial treatment regimen expands the quantity of tumor-reactive NK cells and boosts their functionality in patients.

CD16A is the only activating receptor triggering the cytotoxic activity of naïve human NK cells even in the absence of co-stimulatory signals (Bryceson, et al., 2009; Bryceson, et al., 2006). It is demonstrated in the examples that CD16A activation by a bispecific tetravalent CD30/CD16A tandem diabody elicits potent NK cell cytotoxicity in response to NK cell-resistant CD30⁺ lymphoma cells. Importantly, it is shown in the examples that CD16A engagement by a CD30/CD16A tandem diabody increases the sensitivity of NK cells towards IL-15 or low-dose IL-2. This leads to an amplification of IL-15 and IL-2-dependent NK cell proliferation, resulting in greatly increased numbers of highly functional NK cells. Subsequent to the initial superior NK cell activity towards CD30/CD16A tandem diabody opsonized tumor cells, increased duration of CD30/CD16A tandem diabody exposure results in impaired NK cell cytotoxicity and reduced IFN-γ production. However, this reduction in potency is transient as it can be restored after culturing of such NK cells with IL-2 or IL-15. Remarkably, when pre-activated by a CD30/CD16A tandem diabody through CD16A, these cytokine-cultured NK cells exert enhanced cytotoxicity and IFN-γ production after re-stimulation towards otherwise almost resistant CD30+ and even CD30⁻ lymphoma cells. Such impaired NK cell cytotoxicity which can be re-stimulated by subsequent cytokine treatment results also from other CD16A antigen binding proteins, such as bispecific tandem antibodies like EGFR/CD16A or BCMA/CD16A. Hence, the present invention reveals an unappreciated role for CD16A triggering in priming and amplifying NK cell functions in response to activating cytokines and tumor cells.

The improved sensitivity to IL-15 and low-dose IL-2 coincides with the induction of CD25, the high-affinity IL-2 receptor α-chain, and the up-regulation of CD132, the low-affinity γ-chain, which is part of both the IL-2 and IL-15 receptor. CD25 induction by a CD30/CD16A tandem diabody is significantly stronger than previously shown upon CD16A cross-linking using anti-CD16 3G8 with a secondary antibody (Marquez, et al., 2010). Similarly, NK cell activation by IL-12/15/18 has been shown to induce robust CD25 expression, boosting IL-2-dependent proliferation in vitro and in vivo in tumor-bearing mice (Ni, et al., 2012). Hence, the induction of CD25 after CD30/CD16A tandem diabody exposure enables the NK cells to compete for low amounts of IL-2 with regulatory T cells, which otherwise limit the availability of IL-2 for NK cells due to constitutive CD25 expression (Gasteiger, et al., 2013; Kim, et al., 2017). In addition to CD16A engaging tandem diabody, Fc-mediated engagement of CD16A by rituximab recapitulates the enhanced proliferative potential as well as the transient reduction in potency, indicating a more global phenomenon of CD16A activation. However, the modulations of CD25 and CD16 in response to CD16A engaging tandem diabody are less heterogeneous and more pronounced among healthy donors compared to rituximab. The profound activating potential of CD16A engaging tandem diabody may be attributed to its prolonged and high-affinity bivalent binding to CD16A regardless of CD16A polymorphisms (low or high affinity for Fc domains of IgG antibodies) as compared to Fc-engaging rituximab (Reusch, et al., 2014).

Subsequent to exposure to a CD16A engaging tandem diabody, a transient and selective reduction in potency of CD16A-dependent and even 'natural' NK cell cytotoxicity, degranulation and IFN-γ in the second response to tumor cells is observed. The impairment of CD16A-dependent activity may be explained by the almost complete loss of CD16 expression upon CD16A engagement, which at least in part involves MMP-mediated cleavage, or receptor internalization as additionally described (Capuano, et al., 2015; Lajoie, et al., 2014; Mota, et al., 2004; Romee, et al., 2013; Wiernik, et al., 2013). Besides, the transient reduction in potency of 'naive' NK cells, anti-tumor reactivity suggested a desensitization of other NK cell-activating receptors, such as NKp30 and NKG2D, shown to be involved in K562 lysis (Brandt, et al., 2009; Kuylenstierna, et al., 2011). The reduction in degranulation and IFN-γ production even in response to PMA/ionomycin is indicative of a broader transient reduction in potency that apparently also affects PKC activation and/or $Ca^{2+}$ mobilization, which are directly activated by PMA/ionomycin (Chatila, et al., 1989). $Ca^{2+}$ mobilization is critically involved in the terminal signaling of CD16A and other activating receptors (Bryceson, et al., 2006; Cassatella, et al., 1989). PKC activation can mediate IFN-γ production, and is important for K562 lysis but dispensable for ADCC, which in turn requires PI3K activation (Bonnema, et al., 1994; Hara, et al., 2008).

Hence, the observed transient reduction in potency of primary NK cells after a 20-hour tandem diabody exposure, e.g. CD30/CD16A tandem diabody, may exceed the more limited inhibitory effect which was previously found as a result of short-term (1.5-hour) CD16A engagement; this inhibition was reported to involve SHP-1 recruitment and inhibition of PLCγ2/Vav-1/SLP-76 phosphorylation, resulting in defective degranulation, whereas IFN-γ production and responsiveness to PMA/ionomycin remained unaltered (Capuano, et al., 2015; Galandrini, et al., 2002).

The IFN-γ response to IL-12/15/18 after CD16A engagement is conserved or even further enhanced, indicating that the NK cells after CD16A engaging tandem diabody exposure, e.g. CD30/CD16A tandem diabody, have only a selective reduction in IFN-γ towards activation by tumor cells. This may be explained by the up-regulation of the high-affinity IL-12 and IL-18 receptors, which potently induce IFN-γ. It has been reported that CD16A and IL-12 receptor activation can synergistically promote IFN-γ production (Kondadasula, et al., 2008).

Overall, the transient reduction in NK cell function upon CD16A engaging tandem diabody exposure, e.g. CD30/CD16A tandem diabody, can be fully restored after subsequent culture in IL- or IL-15. Importantly, these CD16A-experienced cytokine-cultured NK cells possess memory-like functionality, since the cytotoxic activity and IFN-γ production towards re-stimulation with otherwise weakly susceptible lymphoma cells is substantially enhanced. Intriguingly, this novel functionality of 'CD16A-induced memory-like NK cells' might be similar to the previously described enhanced anti-tumor activity and IFN-γ response of IL-12/15/18-induced memory-like NK cells (Cooper, et al., 2009; Ni, et al., 2016; Ni, et al., 2012; Romee, et al., 2012; Romee et al, 2016).

This illustrates that an intermittent dosing scheme for an anti-CD16A antigen binding protein, e.g. tandem diabody, comprising an exposure-free period to the antigen binding protein improves the responsiveness of individual NK cells to a repeated encounter of antibody-opsonized tumor cells. Furthermore, the intermittent administration of a CD16A engaging antigen binding molecule with NK cell-activating cytokines like IL-2 or IL-15 according to the invention not only sustains but even enables amplified anti-tumor activity of NK cells, and expands the quantity of tumor-reactive NK cells in lymphoma patients.

INCORPORATION BY REFERENCE

All publications, patents, and patent applications mentioned in this specification are herein incorporated by reference to the same extent as if each individual publication, patent, or patent application is specifically and individually indicated to be incorporated by reference.

DETAILED DESCRIPTION OF THE INVENTION

Figure 1:
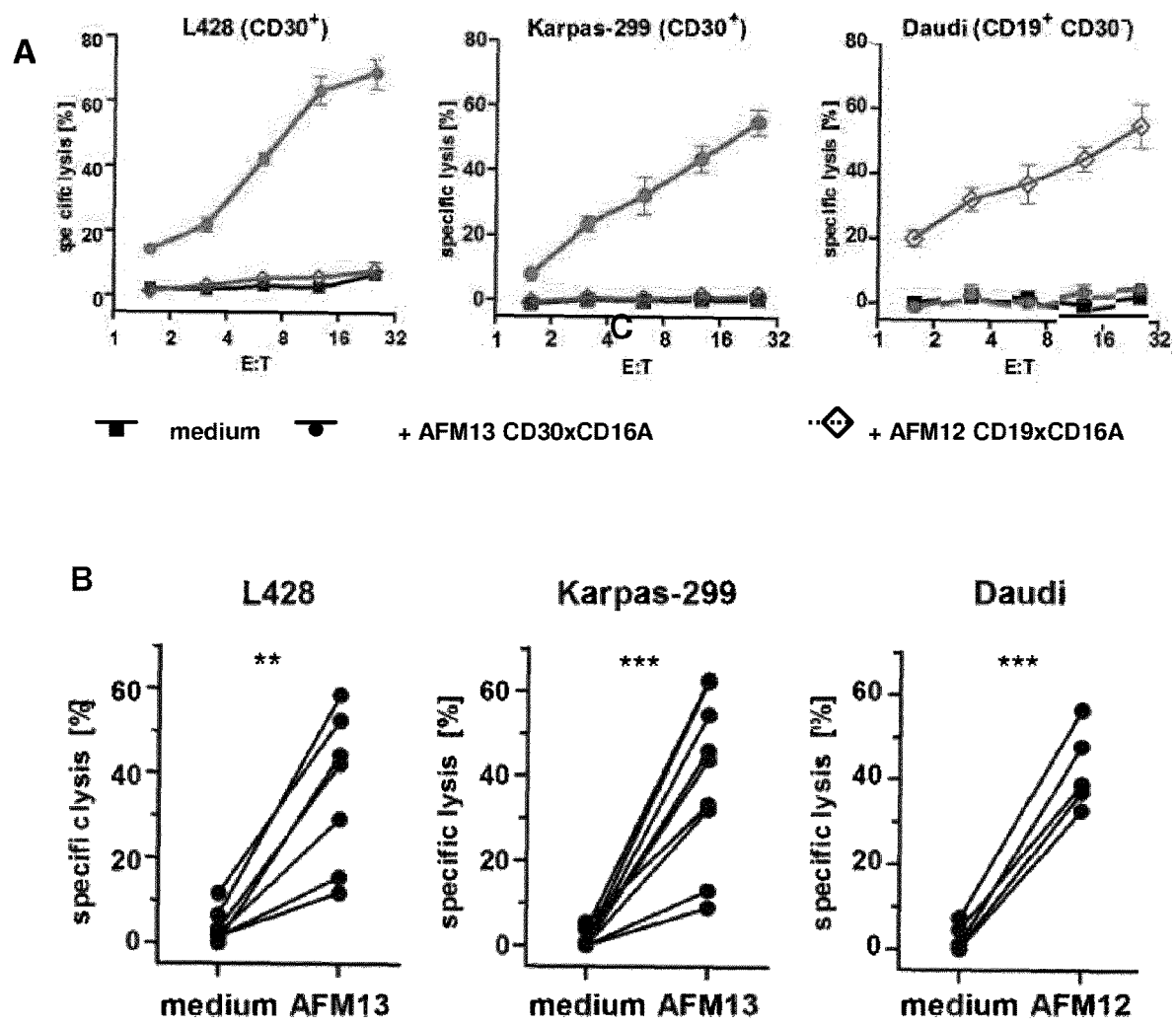
FIG. 1 shows CD30/CD16A tandem diabody-opsonized tumor cells inducing NK cell cytotoxicity, IFN-γ production and activating receptors:
A. Specific lysis of CD30+ CD19+ Karpas-299 and L428 cells, and CD30+ CD19+ Daudi cells by freshly-isolated primary NK cells was measured in 4-hour $^{51}$Cr release assays in the presence of CD16AxCD30 tandem diabody AFM13 (circles), CD16AxCD19 tandem diabody AFM12 (diamonds) (all 10 μg/mL) in comparison to no antibody addition (squares) at increasing effector-target (E:T) ratios; data are representative for at least three experiments. B. Cumulative specific lysis of Karpas-299, L428 and Daudi cells (E:T 6:1) with/without AFM13. C. AFM13-induced lysis (circles) of Karpas-299 and L428 cells by NK cells was compared to lysis induced by a parental chimeric anti-CD30 IgG antibody (triangles) at an antibody concentration range of $10^{-5}$-10 μg/mL (E:T 25:1). AFM12 was used as a negative control (diamonds). D. Specific lysis of Karpas-299 and L428 in the presence of AFM13 (1 μg/mL) was compared between purified NK cells (circles) and whole PBMC (squares) at matched E:T ratios. Lysis by NK cell-depleted PBMC (PBMC ANK) (triangles) was corrected for the absence of NK cells; data are representative for two experiments. E. NK cell CD107a expression (degranulation marker) and intracellular IFN-γ expression was measured by flow cytometry after 4-hour co-culture of purified NK cells and L428 cells (E:T 1:1) with/without AFM13 (0.4 μg/mL) as indicated. IFN-γ production was quantified by ELISA after a 20-hour co-culture; cumulative data of four experiments.
Figure 1:
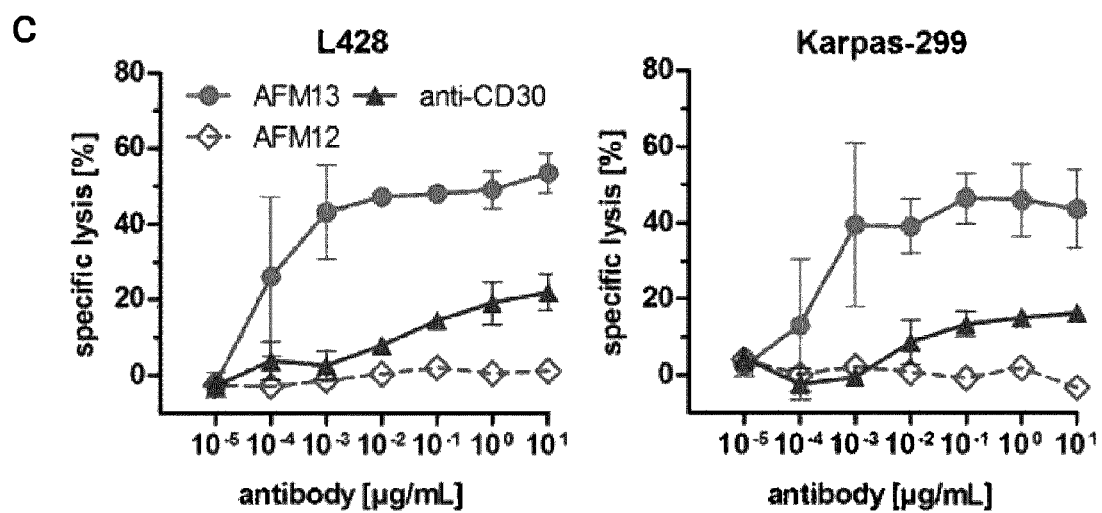
Figure 1:
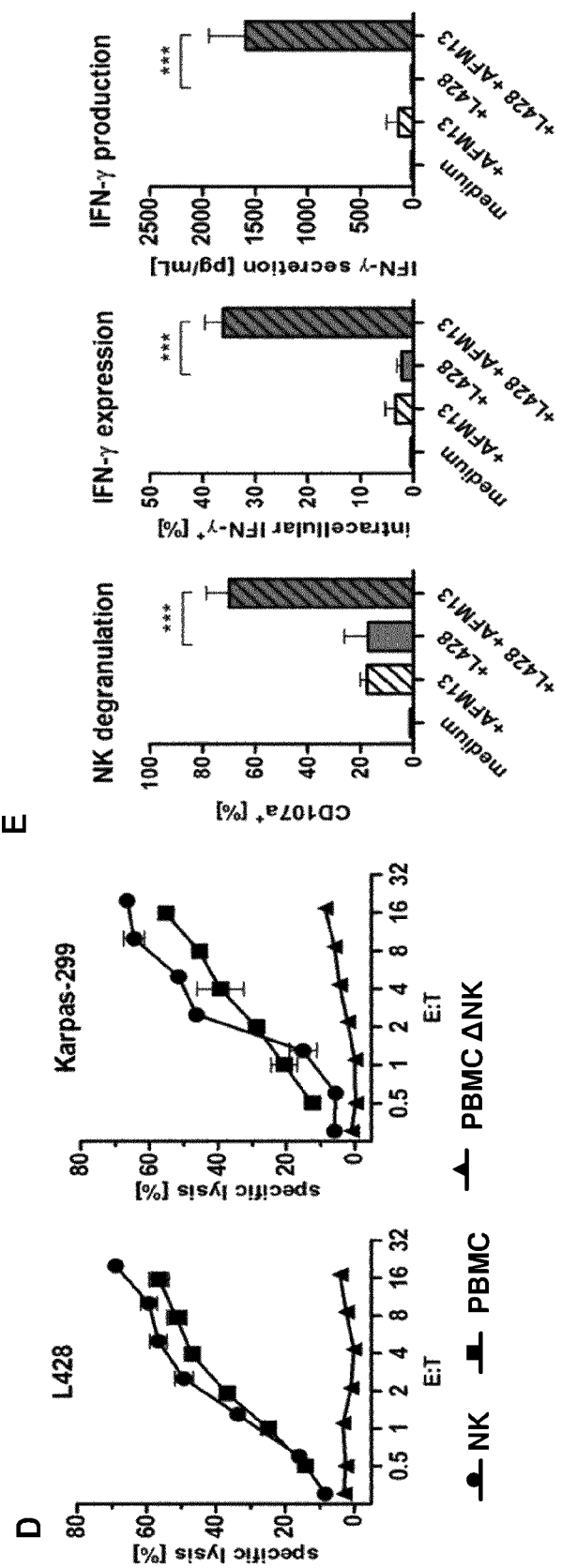

The invention provides an antigen binding protein comprising at least one antigen binding site for CD16A for use in NK cell-based immunotherapy, wherein the antigen binding protein is administered intermittently comprising an exposure free period to the antigen binding protein between two intermittent, i.e. consecutive, doses and, optionally, in combination with a cytokine.

The NK cell-based immunotherapy may be in vivo and/or comprise an ex vivo step, for example, an adoptive NK cell transfer or hematopoietic stem cell transplantation (HCT), in which either autologous NK cells or allogeneic NK cells may be activated by cytokines and expanded ex vivo and then transferred into the patient.

In certain embodiments the antigen binding protein is multivalent and comprises at least two antigen binding sites specific for CD16A which results in bivalent binding to the NK cell through the CD16A receptor, thereby increasing the avidity and the potency for cytotoxic activation of the NK cell.

In certain embodiments the antigen binding protein is multispecific and comprises at least one further antigen binding site specific for a target antigen different from CD16A for engaging the NK cell towards the target, e.g. tumor cell or virus.

In particular embodiments the antigen binding protein is a tetravalent bispecific tandem diabody comprising two antigen binding sites for CD16A and two antigen binding sites for a target antigen, e.g. tumor antigen or viral antigen.

The term "combination" refers to simultaneous, separate or sequential administration of the compounds of the combination, i.e. the CD16A antigen binding protein and cytokine.

The term "subject" as used herein includes an individual, e.g. patient, suffering or afflicted with a disorder to be treated by NK cell-based immunotherapy, for example a cancer or any disorder involving a cancer. In the embodiment of a CD30/CD16A antigen binding protein the disorder is a CD30 positive malignancy, in particular a CD30⁺ lymphoma, such as, for example, Hodgkin's lymphoma, anaplastic large-cell lymphoma (ALCL), diffuse large B-cell lymphoma (DLBCL).

The term "antigen binding protein" denotes an immunoglobulin derivative with antigen binding properties. The antigen binding protein of the invention engages NK cells through binding to CD16A. The antigen binding protein may comprise immunoglobulin polypeptides, fragments thereof, conjugates or fusion peptides of immunologically functional immunoglobulin portions that comprise an antigen binding site. The binding protein comprises at least one antigen binding site which is the region, portion or domain of the binding protein that binds to the antigen. In certain embodiments each antigen binding site is formed by a variable heavy chain domain (VH) and a variable light chain domain (VL) of an immunoglobulin specifically binding to the same antigen epitope. The variable heavy chain domain comprises three heavy chain complementarity determining regions (CDR): CDR1, CDR2 and CDR3. The variable light chain domain comprises three complementarity determining regions (CDR): CDR1, CDR2 and CDR3. In alternative embodiments the antigen binding site may consist only of a heavy chain or a light chain. For example, such antigen binding site may be derived from a nanobody that consists only of a heavy chain and can bind to CD16A in the absence of a light chain. Nanobodies derived from llamas or camels have been described. A VH-based antigen binding site having specificity for CD16A which does not comprise a VL domain has been described (Li et al., 2016). The binding protein may be an IgG-like or non-IgG-like fusion peptide based on Fv domains either without or with additional constant domains. In certain embodiments of the invention the binding protein is devoid of immunoglobulin constant domains. The variable heavy and light chain domains of an antigen binding site may be covalently linked with one another, e.g. by a peptide linker, or non-covalently associate with one another to form an antigen binding site.

In certain embodiments the antigen-binding protein comprises an antigen binding site that binds to CD16A, but not to CD16B. An antigen-binding site comprising heavy and light chain variable domains binding to CD16A, but not binding to CD16B may be provided by an antigen-binding site which specifically binds to an epitope of CD16A which comprises amino acid residues of the C-terminal sequence SFFPPGYQ (SEQ ID NO:11) and/or residues G130 and/or Y141 of CD16A (SEQ ID NO:20) which are not present in CD16B. Examples of antigen-binding sites comprising heavy and light variable chain domains that bind to CD16A, but not to CD16B are described in WO 2006/125668.

In some embodiments the antigen-binding protein comprises a heavy and a light variable chain domain specific for CD16A, wherein (i) the heavy chain variable domain specific for CD16A (VH_CD16A) comprises a heavy chain CDR1 having the amino acid sequence set forth in SEQ ID NO:1; a heavy chain CDR2 having the amino acid sequence set forth in SEQ ID NO:2 or 7; a heavy chain CDR3 having the amino acid sequence set forth in SEQ ID NO:3 and the light chain variable domain specific for CD16A comprises a light chain CDR1 having an amino acid sequence set forth in SEQ ID NO:4; a light chain CDR2 having an amino acid sequence set forth in SEQ ID NO:5; and a light chain CDR3 having an amino acid sequence set forth in SEQ ID NOs:6. In further embodiments the antigen binding protein comprises (a) a heavy chain variable domain specific for CD16A (VH_CD16A) having the amino acid sequence set forth in SEQ ID NOs:8 or 10 and/or (b) a light chain variable domain specific for CD16A (VL_CD16A) having the amino acid sequence set forth in SEQ ID NO:9.

In alternative embodiments, the heavy and light chain domains incorporate immunologically active homologues or variants of the CDR or framework sequences described herein. Accordingly in some embodiments, a CDR sequence in a heavy or light chain domain that binds to CD16A is similar to, but not identical to, the amino acid sequence depicted in SEQ ID NOs: 1-7. In certain instances, a CDR variant sequence has a sequence identity of 99%, 98%, 97%, 96%, 95%, 94%, 93%, 92%, 91%, 90%, 89%, 88%, 87%, 86%, 85%, 84%, 83%, 82%, 81%, or 80% compared to the sequence of SEQ ID NOs: 1-7 and which is immunologically active.

In further instances, a CDR variant sequence incorporates 1, 2, 3, 4, or 5 conserved amino acid substitutions. Conservative substitutions include amino acid substitutions that substitute a given amino acid with another amino acid of similar characteristics and further include, among the aliphatic amino acids interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine.

In other instances, a CDR variant sequence is modified to change non-critical residues or residues in non-critical regions. Amino acids that are not critical can be identified by known methods, such as affinity maturation, CDR walking mutagenesis, site-directed mutagenesis, crystallization, nuclear magnetic resonance, photoaffinity labeling, or alanine-scanning mutagenesis.

In further alternative embodiments, the antigen binding protein comprises heavy and light chain domains that are immunologically active homologues or variants of heavy and light chain domain sequences provided herein. Accordingly, in some embodiments, an antigen binding protein comprises a heavy or light chain domain sequence that is similar to, but not identical to, the amino acid sequence depicted in SEQ ID NOs: 8-10. In certain instances, a variant heavy or light chain domain sequence has a sequence identity of 99%, 98%, 97%, 96%, 950, 94%, 930, 92%, 91%, 900, 890, 880, 87%, 860, 850, 84%, 83%, 82%, 81%, or 80% compared to the sequence of SEQ ID NOs: 8-10 and which is immunologically active.

In further instances, a variant heavy or light chain domain sequence incorporates 1, 2, 3, 4, or 5 conserved amino acid substitutions. Conservative substitutions include amino acid substitutions that substitute a given amino acid with another amino acid of similar characteristics and further include, among the aliphatic amino acids interchange of alanine, valine, leucine, and isoleucine; interchange of the hydroxyl residues serine and threonine, exchange of the acidic residues aspartate and glutamate, substitution between the amide residues asparagine and glutamine, exchange of the basic residues lysine and arginine, and replacements among the aromatic residues phenylalanine and tyrosine.

In yet further instances, a variant heavy or light chain domain sequence incorporates substitutions that enhance properties of the CDR such as increase in stability, resistance to proteases and/or binding affinities to CD16A.

In other instances, a variant heavy or light chain domain sequence is modified to change non-critical residues or residues in non-critical regions. Amino acids that are not critical can be identified by known methods, such as affinity maturation, CDR walking mutagenesis, site-directed mutagenesis, crystallization, nuclear magnetic resonance, photoaffinity labeling, or alanine-scanning mutagenesis.

The antigen binding protein according to the invention has a half-life shorter than a monoclonal antibody or any other antibody formats employing IgG equivalent domains to achieve IgG comparable half-life as well as constructs employing HSA binding to prolong its half-life, in particular an IgG.

"Half-life" refers to elimination half-life which is the period needed for the concentration of antigen binding protein to reach one-half of its initial amount measured in peripheral blood of humans for the applied route of administration (that is i.e. free antibody in serum such as but not limited to intravenous injection or infusion or subcutaneous application).

In certain embodiments the half-life of the antigen binding protein is less than one week, in particular less than 72 h, 48 h, 42 h, 36 h, 24 h, 20 h, 12 h or 6 h. Such short half-lives are favorable for employing the intermittent administration including an exposure free or exposure reduced period according to the invention, because the exposure free period in the interval between two consequent and intermittent doses of the antigen binding protein remains short.

Such short half-life which is significantly shorter than the half-life of a monoclonal antibody enables the intermittent administration regimen according to the invention, because it allows the provision of exposure reduced or free periods after the elimination of the antigen binding protein between two consecutive doses of the antigen binding protein. Such exposure reduced or free period of the antigen binding protein is important for the recovery of the NK cells. The term "exposure reduced" as used herein refers to an amount, i.e. plasma concentration, of the antigen binding protein which is less than one-half of the initial amount of antigen binding protein measured as described above. Hence, the term "exposure low" refers to an amount of antigen binding protein which is reached after a half-life of the antigen binding protein after its administration. For example, the term "exposure reduced" may refer to an amount of less than 40%, 30%, 20%, and 15%, such as 15-40%, 15-30% or 15-20% of the initially administered dose of the antigen binding protein.

The term "exposure free" as used herein refers to an amount, i.e. plasma concentration, of the antigen binding protein which is less than the amount after at least 3 half-lives of the antigen binding protein which corresponds to 15% or less of the administered dose of the antigen binding protein. Preferably, "exposure free" refers to an amount i.e. plasma concentration, of the antigen binding protein which is less than the amount after at least 4 to 5 half-lives of the antigen binding protein. Preferably "exposure free" refers to an amount, i.e. plasma concentration, of the antigen binding protein which is less than 10%, 1% or 0.1% of the administered dose of the antigen binding protein.

An antigen binding protein according to the invention with a significantly shorter half-life than a monoclonal antibody can be provided by recombinant antibody derivatives with—compared to monoclonal antibodies—lower molecular weights.

Examples of antigen binding proteins with a short half-life according to the invention include non-IgG-like antibody fragments or fusion peptides of immunologically functional immunoglobulin portions such as, for example, Fab, Fab', F(ab')2, Fv fragments, e.g. single-chain Fv, tandem single-chain Fv ((scFv)2), Bi-specific Killer Engagers (BiKE), Tri-specific Killer Engagers (TriKE), dual affinity retargeting antibodies (DART™), diabody (Db), single chain diabody (scDb) and tandem diabody (TandAb®), and nanobodies or antigen binding proteins generated by Dock-and-lock (DNL) method; tribody. The antigen binding proteins may be based essentially on Fv domains or, alternatively, also comprise one or more constant antibody domain. Dependent on desired features, such as valency, multispecificity, pharmacokinetic and pharmacodynamic properties Fv and/or constant domains and/or additional functional domains may be modularly assembled in different formats or scaffolds, such that, for example, described in Brinkmann and Kontermann, mAbs, 2017, 9(2):182-192 or in Spiess et al., 2015, Molecular Immunology, 67:95-106. For example, tandem diabodies, such as the CD30/CD16A, BCMA/CD16A or EGFR/CD16A tandem diabodies have a half-life of less than 24h, 22h, or 20h, while a tandem single-chain Fv ((scFv)2) has a half-life of about less than 5h, 4h, 3h or in particular 2h.

Furthermore, the binding protein may be multivalent, i.e. comprises two or more antigen binding sites. In certain embodiments the antigen binding protein comprises at least two antigen binding sites for CD16A, i.e. binds bivalently CD16A. In some embodiments the binding protein comprises a tag-amino acid sequence for purification.

In certain embodiments the antigen binding protein is multispecific and comprises at least one further antigen binding site which binds to a target antigen different from CD16A, i.e. has a second different antigen specificity. In certain embodiments the antigen binding protein may comprise at least two antigen binding sites for the target antigen.

"Target antigen" typically refers to an antigen associated with the site, e.g. cell or virus, to which the NK cell should be directed by the antigen binding protein for triggering NK cell cytotoxicity. Examples of target sites may be tumor cells or infectious agents such as viral or bacterial pathogens or parasites, for example dengue virus, herpes simplex, influenza virus, HIV or cells carrying autoimmune targets, an autoimmune marker or an autoimmune antigen.

The target antigen different from CD16A may be selected from a bacterial substance, viral protein, autoimmune marker or a tumor antigen.

In embodiments where the target antigen is a tumor antigen, the tumor antigen may be selected from tumor cell surface antigens, for example specific tumor markers, or a MHC restricted peptide displayed by an MHC class molecule. The term "tumor antigen" as used herein comprises tumor associated antigen (TAA) and tumor specific antigen (TSA). The term "tumor cell surface antigen" refers to any antigen or fragment thereof capable of being recognized by an antibody on the surface of a tumor cell.

Examples of target antigens for tumor cells include but are not limited to CD5, CD19, CD20, CD30, CD33, matrix metalloproteinase 1 (MMP1), the laminin receptor precursor protein, EGFR, EGFRvIII, BCMA, Ep-CAM, PLAP, Thomsen-Friedenreich (TF) antigen, MUC-1 (mucin), IGFR, IL4-R alpha, IL13-R, FcεRI, IgE, VGEF, HER2/neu, HERS, PSMA, CEA, TAG-72, HPV E6, HPV E7, BING-4, Cyclin-Bi, 9D7, EphA3, Telomerase, Mesothelin, SAP-1, Survivin, Cancer Testis antigens (BAGE family, CAGE family, GAGE family, MAGE family, SAGE family, XAGE family), NY-ESO-1/LAGE-1, PRAME, SSX-2, Melan-A/MART-1, Gp100/pme117, Tyrosinase, TRP-1/-2, MC1R, β-catenin, BRCA1/2, CDK4, CML66, MART-2, p53, Ras, TGF-βRII and TCR (from Categories of Tumor Antigens, Holland-Frei Cancer Medicine. $6^{th}$ edition, 2003). Further tumor antigens are described in Weinberg, R., The Biology of Cancer, 2013.

In certain embodiments the antigen binding protein which is multispecific comprises at least two antigen binding sites for the target antigen. In particular embodiments the antigen binding protein comprises at least two antigen binding sites for CD16A and at least two antigen binding sites for the target antigen. Such an antigen binding protein is at least tetravalent.

In a particular embodiment, a bispecific and tetravalent tandem diabody (TandAb®) is provided. A tandem diabody is constructed by linking the four variable domains of the heavy and light chains (VH and VL) from two or more different Fv domains in a single polypeptide. These domains are positioned such that corresponding VH and VL can pair when two molecules of the polypeptide align in a head-to-tail fashion. Short linkers between the domains (twelve or fewer amino acids) prevent intramolecular pairing of the Fv. The tandem diabody and its manufacture is described in Weichel et al., 2015; Kipriyanov S M, 2009 or Kipriyanov S M, 2003.

Exemplified in the examples is, among others, the bispecific and tetravalent CD30/CD16A tandem diabody AFM13 having specificity for CD30 and CD16A (CD30/CD16A tandem diabody), which has been described in Reusch, et al., 2014. This CD30/CD16A tandem diabody specifically recruits NK cells by binding exclusively to the isoform CD16A. The CD30 and CD16A bispecific tandem diabody described herein is designed to allow specific targeting of $CD30^+$ tumor cells by recruiting cytotoxic NK cells. In such tandem diabody, the linker length is such that it prevents intramolecular pairing of the variable domains so that the molecule cannot fold back upon itself to form a single-chain diabody, but rather is forced to pair with the complementary domains of another chain. The domains are also arranged such that the corresponding VH and VL domains pair during this dimerization. Following expression from a single gene construct, two identical polypeptide chains fold head-to-tail forming a functional non-covalent homodimer of approximately 105 kDa. Despite the absence of intermolecular covalent bonds, the homodimer is highly stable once formed, remains intact and does not revert back to the monomeric form.

Tandem diabodies contain only antibody variable domains and therefore are contemplated to lack side effects or non-specific interactions that may be associated with an Fc moiety. For example, Fc receptors are found on numerous cell types such as white blood cells or Kuppfer cells which can bind to $Fc_{gamma}$. Because tandem diabodies allow for bivalent binding to each of the target antigens, e.g., CD30, and CD16A, the avidity is the same as that of an IgG. The size of a tandem diabody, at approximately 105 kDa, is smaller than that of an IgG, which may allow for enhanced tumor penetration. However, this size is well above the threshold for first-pass renal clearance, offering a pharmacokinetic advantage compared with smaller bispecific formats based on antibody-binding domains or non-antibody scaffolds. The half-life of a tandem diabody, such as the CD30/CD16A tandem diabody AFM13, is about 19 hours. Tandem diabodies are well expressed in host cells, for example, mammalian CHO cells. It is contemplated that a robust upstream and downstream manufacturing process is available for tandem diabodies.

The "intermittent" administration as used herein is a method of administering the antigen binding protein in intervals, in particular regular intervals. Hence, a first dose of the antigen binding protein is administered and a second dose of the antigen protein is administered subsequently to the first dose. Preferably, the interval of administration of the first and the second dose is several times repeated for one treatment cycle. The interval between two consecutive doses of the antigen binding protein is selected such that the exposure to the antigen binding molecule based on the pharmacokinetic features, e.g. half-life, of the antigen binding protein is intermittent, thereby allowing at least an exposure reduced or, preferably, an exposure free period between two consecutive doses. Exposure of the anti-CD16A antigen binding protein may transiently reduce potency of NK cells. For efficient recovery of NK cells' cytotoxicity it is important that the exposure, i.e. concentration, of the anti-CD16A antigen binding protein is kept low or absent during the recovery phase. Therefore, the interval is selected such that its period is longer than the half-life of the antigen binding protein for ensuring that the interval comprises an exposure reduced or free period after the antigen binding protein has been mostly eliminated.

Hence, the interval of the intermittent administration is a multiple of the half-life of the antigen binding protein.

In some embodiments the interval may be at least one day longer than the half-life of the antigen binding protein.

In certain embodiments that interval is at least three times the half-life of the antigen binding protein. For example the interval may be at least three to at least five times the half-life of the antigen binding protein, e.g. at least 3, 3.5, 4, 4.5 or 5 times. In the context of the invention the CD16A antigen binding protein is considered as diluted or absent after at least 3 times, preferably 4 to 5 times, of its half-life.

In certain embodiments the interval between two consecutive doses of the CD16A antigen binding protein may be at least 1, 2, 3, 4, 5, 6, 7, 8, 9 or 10 days, wherein the interval depends on the half-life, of the antigen binging protein and is selected such that it comprises an exposure reduced or free period of the antigen binding protein. In particular embodiments, the antigen binding protein is administered intermittently in dosing cycles of consecutive doses, i.e. a first dose and a subsequent second dose, wherein the interval between two consecutive doses is at least 3 days.

Preferably, the dosing cycle comprising a first and a subsequent second dose of the antigen binding protein is repeated multiple times for example 2, 3, 4, 5, 6, 7, 8, 9, 10 or more times, until a desired treatment cycle is completed and/or as long as disease progression is diagnosed and/or until a pre-defined clinical endpoint is achieved, e.g. 4 weeks or 8 weeks or 6 months.

The invention provides a method comprising the step of intermittently administering an anti-CD16A antigen binding protein as described herein and a further step of administering at least one cytokine. Hence, the invention provides an anti-CD16A antigen binding protein as described herein for use in a NK cell-based immunotherapy, wherein the anti-CD16A antigen binding protein is intermittently administered and, further, at least one cytokine is administered.

The cytokine is an NK cell activating cytokine and may be selected from the family of interleukins. The term "cytokine" as used herein is to be understood as a single kind of cytokine or a combination of different kinds of cytokines, wherein a combination of cytokines may be administered simultaneously, separately or sequentially. Hence, the cytokine may be administered prior, simultaneously or subsequently to a dose of the antigen binding protein. This includes multiple repeated doses of cytokines prior or following administration of antigen binding protein. While the antigen binding protein is to be administered intermittently, the cytokine may be administered continuously or intermittently. In the latter embodiments the antigen binding protein and the cytokine may be administered intermittently. In embodiments, in which the antigen binding protein and the cytokine are administered intermittently the time and interval of the administrations of the antigen binding protein and the cytokine may be different; hence, the antigen binding protein and the cytokine are not administered simultaneously.

Thus, the cytokine may be administered subsequently to each administration of the antigen binding protein or a cycle of two or more subsequent administrations of the cytokine may follow an administration of the antigen binding protein. For example, the amount of activated NK cells can be increased by administering a low dose of IL-2 subsequent to a pre-treatment by the antigen binding protein.

For example, the cytokine may be selected from the group consisting of interleukin 2 (IL-2), interleukin 6 (IL-6) interleukin 12 (IL-12), interleukin 15 (IL-15), interleukin 18 (IL-18), interleukin 21 (IL-21) or a combination thereof. In certain embodiments the cytokine is IL-2 or IL-15 or a combination of IL-12, IL-15 and IL-18, in particular, a combination of IL-2 and IL-15. Preferably, IL-2 is administered as a "low dose". A suitable low dose of IL-2 is an amount of about less than 6.0 million units/m$^2$/day subcutaneously (Lissoni P; 1993; Romee et al., 2016).

The low dose administration of IL-2 reduces the risk of undesired side effects of IL-2, such as activation of Tregs, and increases the number of active NK cells, thereby increasing the therapeutic efficacy in the patient. Interleukins for activating NK-cells are reviewed in Romee, R et al., 2014.

The term "cytokine" also refers to compositions and/or agents comprising a cytokine for providing enhanced cytokine mediated immune function. Such agents have been developed to further reduce side effects and modulate distribution and/or pharmacokinetics of cytokine administration. For example, cytokines are provided in complexes with increased biological activity and enhanced half-life. Such complexes may be administered in an antibody like dosing regimen, e.g., once per week. Examples of such cytokine complexes which can be used as cytokine according to the invention are NKTR-214, a biologic pro-drug comprising IL-2 bound to PEG chains (Charych, D., et al., 2016), NKTR-255, a biologic pro-drug comprising IL-15 bound to PEG chains (Nektar Therapeutics, San Francisco, USA) or ALT-803, a multimeric complex constructed by fusing IL-15 super antagonist (IL-15N72D) to the extracellular IL-15Rα sushi domain (IL-15RαSu) (Liu, B et al., 2016)

In a particular embodiment, there is provided a multispecific, e.g. bispecific, antigen binding protein which binds bivalently to CD16A for use in an immunotherapy, e.g. NK cell-based immunotherapy, wherein the antigen binding protein is administered to a subject intermittently. For example that antigen binding protein may be a tandem diabody such as, for example a CD30/CD16A, EGFR/CD16A or BCMA/CD16A tandem diabody.

In further embodiments the antigen binding protein which binds to CD16A is to be administered to a subject intermittently and in combination with a cytokine. The cytokine may be administered alternating with the antigen binding protein or continuously with repeated, i.e. intermittent, doses of the antigen binding protein. In certain embodiments the period or interval between the first dose of the antigen binding protein and the subsequent dose of a cytokine may be adjusted to the elimination (half-life) of the antigen binding protein. Hence, in such embodiments the dose of a cytokine is to be administered after the majority of the antigen binding protein has been eliminated and the half-life time of the antigen binding protein has passed. The administration of the cytokine is intended to restimulate NK cells after exposure to the antigen binding protein. Therefore, the dose of a cytokine should be administered after the antigen binding protein is largely eliminated.

Hence, the antigen binding protein comprising at least one antigen binding site for CD16A for use in NK cell-based immunotherapy can be administered intermittently in a dosage cycle comprising the steps of:
(a) administering a first dose of the CD16A antigen binding protein; and
(b) administering a second dose of the CD16A antigen binding protein,
and the dosage cycle further comprises the administration of at least one cytokine, i.e. a step (c) of administering a dose of at least one cytokine during the interval from step (a) to step (b). Preferably, the second dose of the CD16A antigen binding protein is administered subsequent to step (a) after at least 3 times the half-life of the antigen binding protein.

In particular embodiments, where the cytokine is administered subsequent to a dose of the antigen binding protein, the cytokine is administered at least 20h after the first dose of the antigen binding protein. Hence, the cytokine may be administered—dependent on the half-life of the antigen binding protein—at least 20 h, 24 h, 30 h, 36 h, 42 h, 48 h, 54 h, 60 h, 70 h, 80 h, 90 h or 100 h after the first dose of the antigen binding protein. In particular embodiments, where the antigen binding protein is a tandem diabody and an exposure free period is desired the cytokine may be administered at least about 80-100 h after the first dose of tandem diabody. In other embodiments the cytokine may be administered about 20-36 h after the first dose of the tandem diabody which exposure is already reduced at this time.

For example, the antigen binding protein and the cytokine are to be administered in a dosage cycle comprising the steps of:
(a) administering a first dose of the antigen binding protein;
(b) administering at least one cytokine subsequent to step (a); and
(c) administering a second dose of the antigen binding protein subsequent to step (b).

This dosage cycle can be repeated, preferably at least until progressing disease is diagnosed and/or a desired clinical endpoint is achieved.

The interval between two consecutive administrations of the antigen binding protein (steps (a) and (c)) is for restimulating the potency of NK cells. In certain embodiments the time of administering the cytokine in step (b) is at least after the half-life of the first dose of antigen binding protein of step (a).

The short half-life of the antigen binding proteins according to the inventions warrants the application of the intermittent administration regimen. For the restimulation of NK cells by a subsequent dose of a cytokine it is necessary that the previous dose of antigen binding protein has been largely eliminated so that the NK cells are not exposed to the antigen binding protein any longer. Consequently, the use of an antigen binding protein having a half-life of less than 48h, in particular less than 24h, ensures the intermittent administration regime described herein. The half-life of a tandem diabody, such as the CD30/CD16A tandem diabody AFM13 described herein is about 19h in humans (Rothe, et al., 2015). Hence, according to the invention the dose of cytokine may be administered at least 19h, e.g. 20h, after the administration of the first dose of CD30/CD16A tandem diabody. Alternatively, other antigen binding formats, e.g. such as antibody fragments or single-chain or multi-chain Fv constructs, may be used which have a half-life of less than 19h. Alternatively, the cytokine may be administered prior or simultaneously with a dose of the antigen binding protein or the cytokine may be administered continuously. Hence, the cytokine may be present in the background during the exposure to the CD16A antigen binding protein. However, for the recovery of the NK cell cytotoxicity it is necessary that the dosage cycle between (a) the first dose of the antigen binding protein and (b) the second dose of the antigen binding protein also comprises a respective exposure reduced or, preferably, free period essentially without the antigen binding protein.

In certain embodiments the antigen binding protein is a bispecific and tetravalent tandem diabody, i.e. CD30/CD16A tandem diabody, e.g. AFM13 (Reusch, et. al., 2014). In these embodiments the CD30/CD16A tandem diabody is used for the treatment of CD30$^+$ cancer, for example Hodgkin lymphoma.

Therefore, provided herein are in certain medical uses and methods wherein the antigen binding protein specific for CD30 and CD16A, e.g. CD30/CD16A tandem diabody, as described herein above is administered in an effective dose to a subject for the treatment of a CD30$^+$ cancer, e.g. Hodgkin lymphoma and the like. Hodgkin lymphoma includes newly diagnosed, relapsed, recurrent or refractory Hodgkin lymphoma.

The new intermittent dosage regimen described herein is used in an immunotherapeutic approach of antibody-mediated engagement of NK cells. Such NK cell-based immunotherapy can be used for the treatment of tumors, autoimmune diseases or viral infections.

The NK cell therapy according to the invention may comprise a step of ex vivo stimulation of NK cells. For this step either autologous NK cells may be collected from the subject to be treated or allogeneic NK cells may be collected from a donor. Sources of allogeneic NK cells maybe peripheral blood mononuclear cells (PBMC), cord blood, stem cell differentiation, or "off-the-shelf" lineage NK cell lines (e.g. NK-92 cell line and derivatives thereof).

After purification, the NK cells are expanded ex vivo in accordance with described protocols including feeder cell stimulation, cytokine cocktails, for example including IL-2, IL-12, IL-15, IL-18, IL-21 and combinations thereof. After infusion, these expanded cells are treated with supportive low dose IL-2, IL-15 (Koehl et al, 2016 and Romee et al, 2016) or super agonists such as Altor-803. Comparable procedure is applied to autologous NK cells. The clinical output of such adoptive transfer of NK cells might benefit from tumor targeting by target specific NK cell antigen binding proteins. Effects of the anti-CD16A antigen binding protein are expected to be equivalent for endogenous and adoptively transferred (autologous and allogeneic) NK cells.

Administration is effected by different ways, e.g. by intravenous, intraperitoneal, subcutaneous, intramuscular, topical or intradermal administration. The dosage of binding protein and the interleukin will be determined by the attending physician and other clinical factors. Dosages for any one subject depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology. An "effective dose" useful for treating and/or preventing Hodgkin lymphoma can be determined using known methods.

The examples below further illustrate the described embodiments without limiting the scope of the invention:

Example 1

NK Cell Isolation and Culture

PBMC were isolated from buffy coats of healthy adult donors (Blutbank Mannheim, Germany) by Ficoll-Hypaque density gradient (density 1.077, Biochrom, VWR) or Lymphoprep density gradient (Stem Cell Technologies, cat.: 07861) centrifugation. NK cells were purified from PBMC by negative selection using the "Human NK cell Isolation Kit" (Miltenyi Biotec) or the "MojoSort™ Human NK cell Isolation Kit" (Biolegend) using LS separation columns (Miltenyi Biotec). To deplete NK cells from PBMC (PBMC ANK), CD56 MicroBeads were used for positive selection (Miltenyi Biotec). Freshly-isolated NK cells, hereafter referred to as 'naïve') were maintained overnight in SCGM medium (CellGenix) containing 10% human serum (Invitrogen); PBMC and PBMC ANK in complete RPMI medium.

Alternatively the isolated PBMCs were cultured in RPMI 1640 medium supplemented with 10% FCS (Invitrogen, 10270-106) over-night. For the enrichment of NK-cells PBMC were harvested from overnight cultures and used for one round of negative selection using the EasySep™ Human NK-Cell Enrichment Kit (Stem Cell Technologies, cat.: 17955).

NK Cell Activation by Tandem Diabody (CD30/CD16A, EGFR/CD16A or BCMA/CD16A

NK cells were co-cultured with $CD30^+$ Karpas-299 or L428 cells at 1:1 ratio (each $1\times10^6$ cells) in 24-well plates in the presence of AFM13 (CD30/CD16A) or AFM12 (CD19/CD16A) at 0.1-1 µg/mL for 20 h in complete RPMI medium. Alternatively, NK cells were cultured in 24-well plates (not treated for tissue culture) coated with 0.5 µg/well (10 µg/mL per 0.5 mL PBS coated overnight) of AFM13, rituximab (MabThera; Roche), EGFR/CD16A tandem diabody, BCMA/CD16A tandem diabody or murine IgG1 (not engaging human CD16A; Biolegend) in PBS for 20 h. When indicated, NK cells were treated with IL-2 (12.5-400 U/mL, NIH or Sigma), IL-15 (0.6-10 ng/mL, Peprotech) or a combination of IL-12 (10 ng/mL, Peprotech), IL-15 (20 ng/mL) and IL-18 (100 ng/mL, MBL), hereafter referred to as IL-12/15/18, and cultured in complete SCGM medium for 2-5 days.

NK Cell Proliferation and Numbers

NK cell cultures were loaded with 2 µM CFSE (Sigma-Aldrich), incubated at room temperature for 15 min in the dark and afterwards washed in 5 mL pure FCS and 5 mL RPMI medium. NK cells were then cultured with single-dose IL-2 (12.5-400 U/mL) or IL-15 (0.6-10 ng/mL) at low $0.5\times10^6$/mL cell densities in 24-well plates in complete SCGM medium for 3-7 days. CFSE expression was measured by flow cytometry. CFSE dilution was quantified by calculating the percentage of NK cells that underwent 4 divisions, as derived from CFSE dilution peaks. Absolute NK cell numbers to evaluate NK cell expansion were obtained by counting trypan-blue-negative and life-gated cells by microscopy and by flow cytometry (relative to counting beads), respectively.

$^{51}Cr$ Release Assay, Degranulation and IFN-γ

In the $^{51}Cr$ release assay, NK cells were co-cultured for 4 hours with $^{51}Cr$-labeled target cells in the presence of AFM13, AFM12, EGFR/CD16A tandem diabody, BCMA/CD16A tandem diabody or chimeric anti-CD30 IgG antibody. For degranulation and intracellular IFN-γ expression, NK cells were co-cultured without/with target cells at 1:1 ratio (each $5\times10^4$ cells), antibodies, IL-12/15/18 or PMA (50 ng/mL) with ionomycin (1 mM) in round-bottom 96-well plates for 4 hours in the presence of anti-CD107a-PE (Biolegend) and GolgiPlug (1/100 v/v, BD Bioscience). Extracellular CD107a (marker for degranulation) and intracellular IFN-γ expression was measured by flow cytometry.

Secretion of IFN-γ into cell supernatants was analyzed after 24-hour co-culture of NK cells with tumor cells (1:1 ratio) or IL-12/15 using the human IFN-γ "ELISA MAX" kit (Biolegend).

4 h Calcein-Release Cytotoxicity Assays

For calcein-release cytotoxicity assays the indicated target cells were harvested from cultures, washed with RPMI 1640 medium without FCS, and labeled with 10 µM calcein AM (Invitrogen/Molecular Probes, cat.: C3100MP) for 30 min in RPMI medium without FCS at 37° C. After washing the labeled cells were resuspended in complete RPMI medium (RPMI 1640 medium supplemented with 10% heat-inactivated FCS, 4 mM L-glutamine, 100 U/mL penicillin G sodium, 100 µg/mL streptomycin sulfate). $1\times10^4$ target cells were seeded together with primary human NK-cells at an E:T ratio of 2.5:1 and the indicated antibodies in individual wells of a round-bottom 96-well micro plate in a total volume of 200 µL/well in duplicates. Spontaneous release, maximal release and killing of targets by effectors in the absence of antibodies were determined in quadruplicate on each plate.

After centrifugation for 2 min at 200 g the assay was incubated for 4 h at 37° C. in a humidified atmosphere with 5% $CO_2$. 100 μL cell culture supernatant were harvested from each well after an additional centrifugation for 5 min at 500 g, and the fluorescence of the released calcein was measured at 520 nm using a fluorescence plate reader (EnSight, Perkin Elmer). On the basis of the measured counts, the specific cell lysis was calculated according to the following formula: [fluorescence (sample)−fluorescence (spontaneous)]/[fluorescence (maximum)−fluorescence (spontaneous)]×100%. Fluorescence (spontaneous) represents the fluorescent counts from target cells in the absence of effector cells and antibodies and fluorescence (maximum) represents the total cell lysis induced by the addition of Triton X-100.

Flow Cytometry

Intracellular staining of IFN-γ and perforin/granzyme B was performed after extracellular staining using the "FoxP3 Staining Buffer Set" (eBiosciences) and the "Cytofix/Cytoperm" kit (BD Bioscience), respectively. Samples were acquired on a FACS Calibur or Canto II (BD Bioscience) and analyzed with FlowJo 10 software (FlowJo LLC).

Surface marker expression on NK cells was determined using CD45 PerCpCy5.5 (BD Bioscience; 558411), CD16 BV421 (BioLegend; 302038), CD56 PC7 (Beckman Coulter; A21692) and the fixable viability dye eF780 (eBioscience; 65-0864-14). Samples were acquired on a CytoFLEX S (Beckman Coulter) and analyzed using the CytExpert 2.1 software.

Example 2

CD30/CD16A Tandem Diabody (AFM13) Induces Functional and Phenotypic Activation of NK Cells in Response to CD30+ Lymphoma Cells The presence of bispecific tetravalent tandem diabody AFM13 (CD30/CD16A) significantly improved the cytotoxic activity of freshly-isolated NK cells towards CD30+ cancer cell lines of classical Hodgkin lymphoma, anaplastic large cell lymphoma and non-Hodgkin lymphoma in 4-hour $^{51}$Cr release assays (FIG. 1, A). This was particularly evident against CD30+ tumor cells resistant to naïve NK cells. In contrast, lysis of CD30+ cells remained unchanged by AFM13 tandem diabody while lysis of CD19+ CD30+ Daudi cells could be increased by AFM12 tandem diabody (CD19/CD16A). AFM13 tandem diabody was effective at concentrations of as low as $10^{-3}$ μg/mL and was several orders of magnitude more potent than a conventional anti-CD30 IgG1 antibody (FIG. 1, C). Overall, the percentage of AFM13-mediated lysis was comparable between purified NK cells and PBMC at matched NK cell-target ratios, whereas NK cell-depleted PBMC were unable to induce tumor cell lysis (FIG. 1, D).

AFM13-mediated NK cell cytotoxicity could be potentiated by a 2-day pre-activation of NK cells with IL-2, IL-15 or IL12/15/18, especially against tumor cells weakly susceptible to cytokine-activated NK cells. Interestingly, the interaction of NK cells with AFM13-opsonized target cells induced lysis of bystander non-opsonized CD30+ (but not CD30+) tumor cells, which was not observed after interaction with K562 or cetuximab-opsonized target cells that potently activate NK cells.

Thus, lysis of bystander CD30+ tumor cells strictly required AFM13 tandem diabody and was likely due to residual AFM13 tandem diabody bound to CD16A on NK cells.

Example 3

CD30/CD16A Tandem Diabody (AFM13)-Pre-Activation Through CD16A Amplifies NK Cell Proliferation in Response to IL-15 or Low-Dose IL-2

Figure 2:
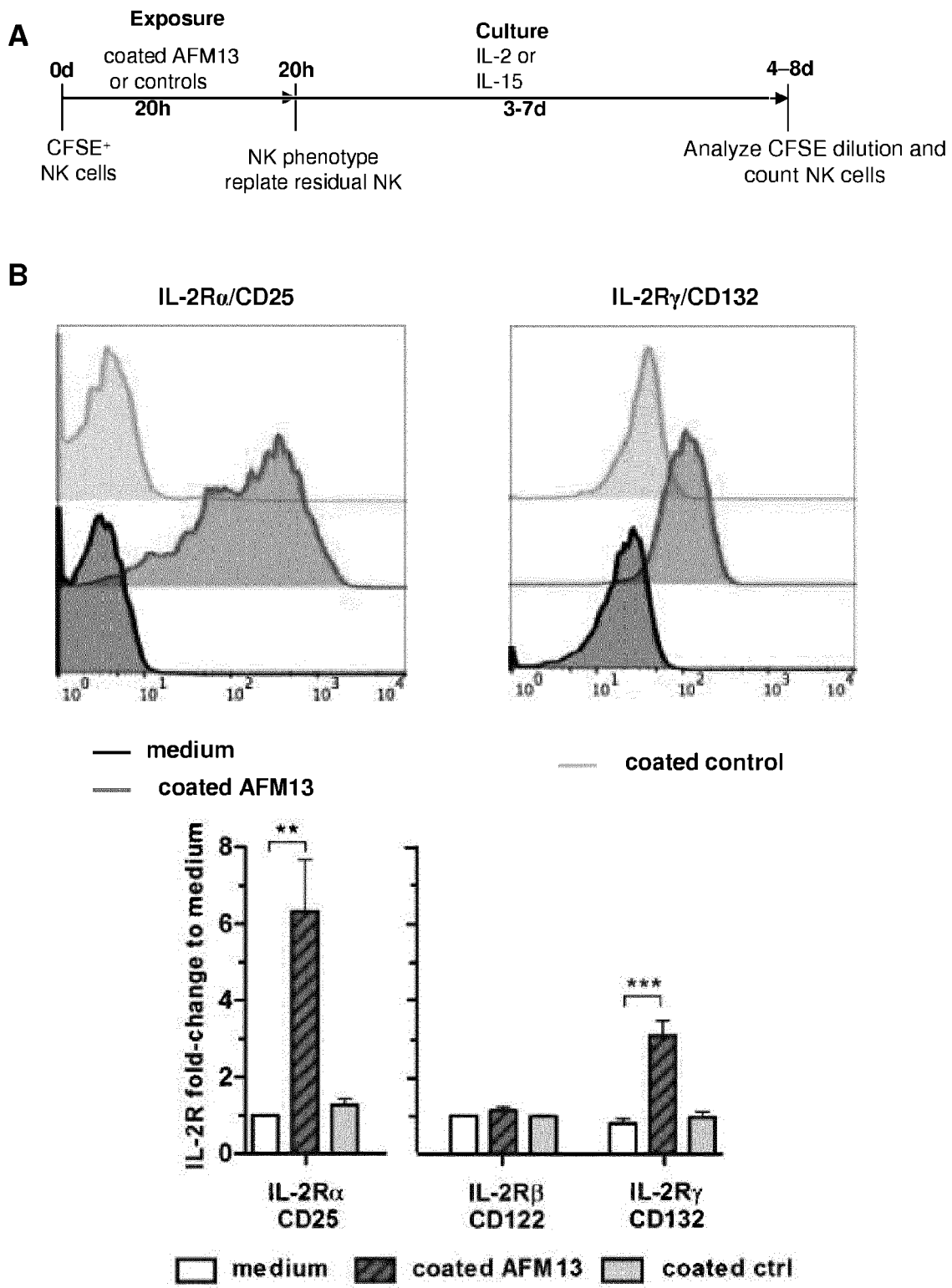
FIG. 2 shows that pre-activation through CD16A by CD30/CD16A tandem diabody increases NK cell proliferation and expansion in response to IL-15 or low-dose IL-2: A. Scheme of the experimental setup. B. Expression of CD25, CD122 and CD132 after 20-hour culture of NK cells in medium or on plastic-coated (coated) AFM13 (1 μg/well) (referred to as AFM13-pre-activation), depicted as representative histograms and fold-change compared to medium (cumulative data of five experiments). Coated mouse IgG1 was used as a negative control (coated ctrl). C. After culture in medium or on coated AFM13, CFSE-labeled NK cells were harvested, replated and incubated with IL-2 (400 U/mL) for 3-7 days; afterwards, CFSE expression was measured by flow cytometry; representative data for two experiments (MFI values indicated). D. Percentage of NK cells that underwent at least four divisions (calculated by CFSE dilution) assessed after 5-day culture in IL-2 (400 U/mL) subsequent to AFM13-pre-activation or medium; cumulative data of five experiments. E. CFSE expression and absolute NK cell numbers after 5-day culture at escalating concentrations of IL-2 (12.5-400 U/mL) or F. IL-15 (0.6-10 ng/mL) of AFM13-pre-activated NK cells or control NK cells; Data of two experiments.
Figure 2:
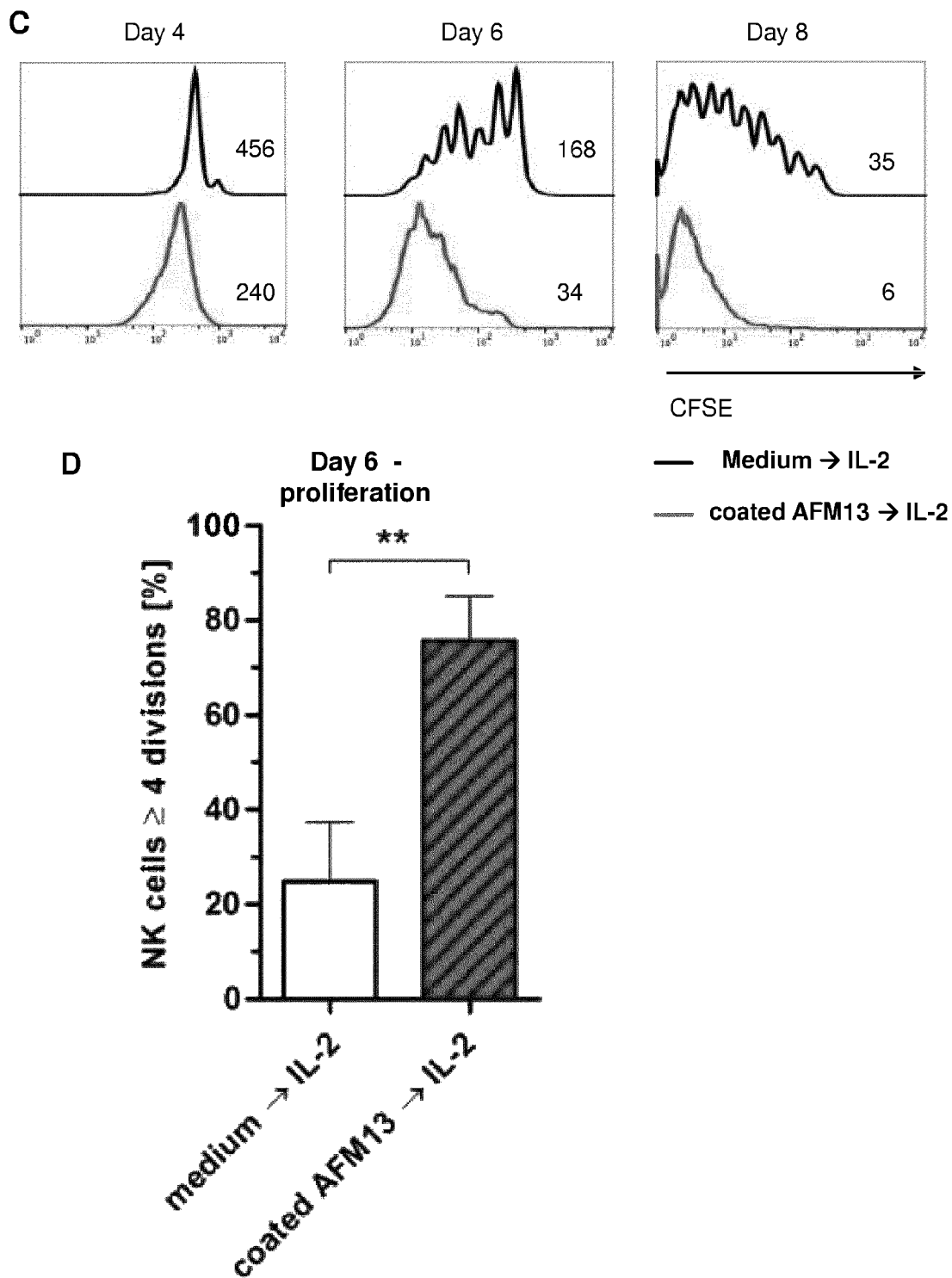
Figure 2:
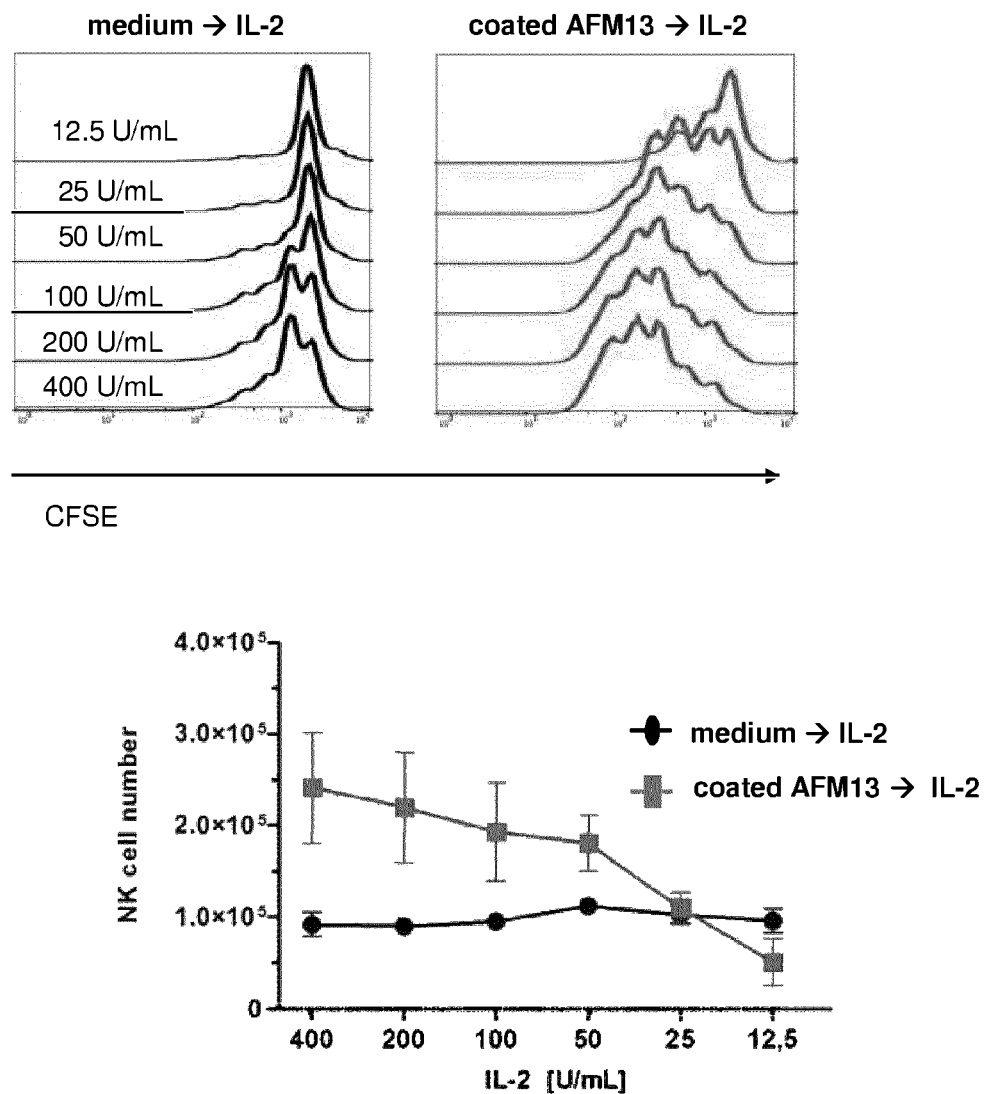
Figure 2:
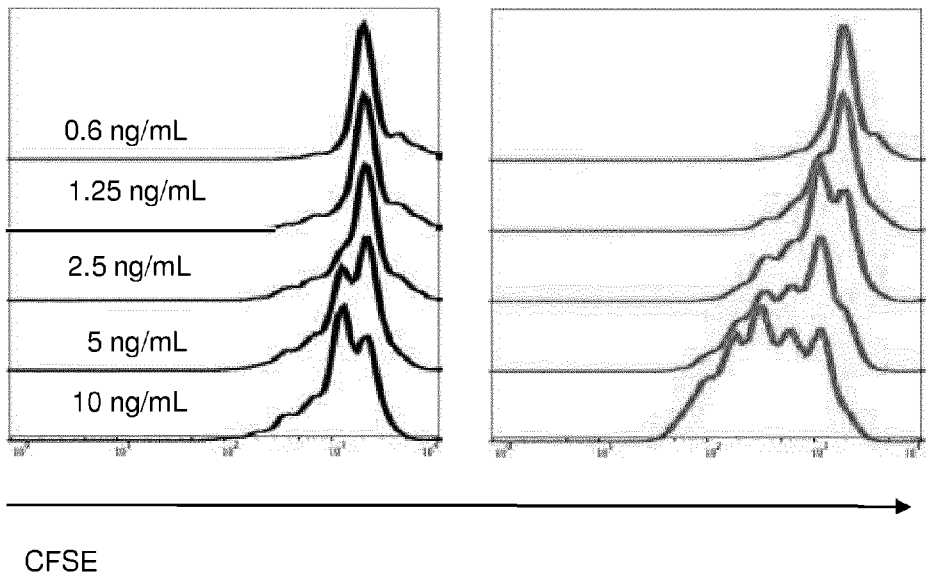
Figure 2:
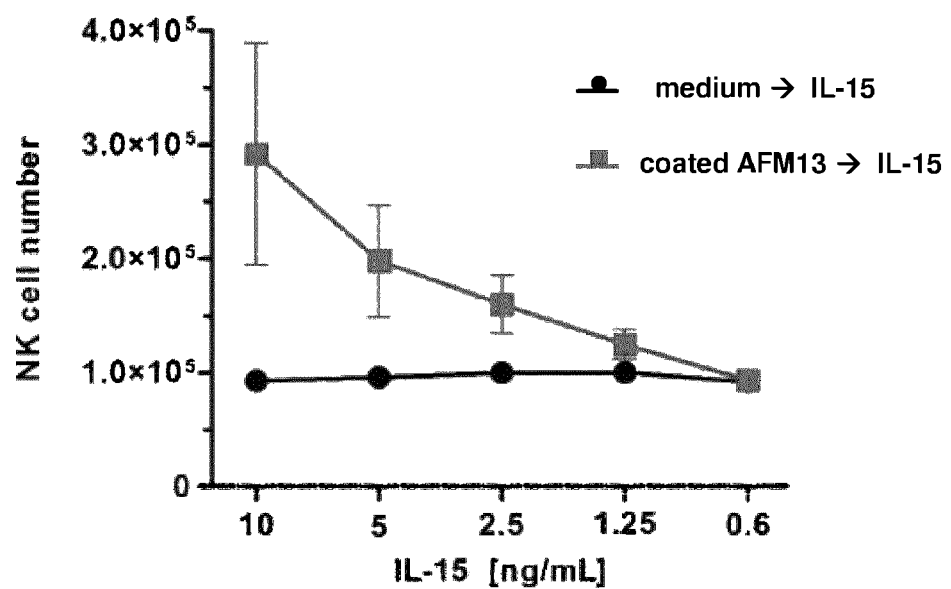

In response to AFM13-opsonized tumor cells up-regulation of CD25 (IL-2Rα) and CD132 (IL-2Rγ) on NK cells implied improved IL-2-dependent functions. Therefore, the pre-activation by AFM13 enhanced IL-2-dependent NK cell proliferation was investigated. CFSE-labeled NK cells were incubated in a tumor-free system on coated AFM13 for 20 h, replated and incubated with IL-2 for 3-7 days (FIG. 2, A). At the applied low cell densities, cytokines alone are a weak stimulus for NK cell proliferation. Analogous to the response to AFM13-opsonized tumor cells, exposure to coated AFM13 resulted in the up-regulation of CD25 and CD132 on NK cells while the expression of CD122 (IL-2Rβ) remained unchanged (FIG. 2, B). Remarkably, AFM13 tandem diabody pre-activated NK cells displayed a marked dilution of CFSE after culture in IL-2 which became most evident on day 5 and increased further to day 7 (FIG. 2, C). In contrast, NK cells which were previously exposed to no AFM13 tandem diabody or soluble AFM13 tandem diabody displayed considerably less CFSE dilution (FIG. 2, C; data not shown). The percentage of NK cells that underwent at least four divisions was significantly higher in AFM13-pre-activated NK cells, indicating enhanced IL-2-mediated proliferation after AFM13 tandem diabody exposure (FIG. 2, D). Similar results were obtained after exposure to rituximab, binding CD16A through its human Fc portion.

Next, it was assessed whether AFM13-mediated pre-activation alters the sensitivity to low doses of IL-2. In fact, even at a low concentration of 50 U/mL, AFM13-pre-activated NK cells showed a comparable marked dilution of CFSE as a higher dose of 400 U/mL, while the minimal concentration to amplify proliferation was 25 U/mL (FIG. 2, E). In addition, absolute NK cell numbers were substantially increased after culture in low and high doses of IL-2, resulting in an up to 4-fold expansion of NK cell numbers. Similarly, IL-15-mediated NK cell proliferation and absolute NK cell numbers were enhanced after AFM13 pre-activation; however, this effect was mainly observed at the highest tested dose of IL-15 (10 ng/mL) (FIG. 2, F).

Hence, CD16A engagement of naïve NK cells by AFM13 tandem diabody or rituximab resulted in an up-regulation of CD25 and CD132, leading to enhanced responsiveness of NK cells to IL-15 and low doses of IL-2, which amplified IL-2 and IL-15-mediated NK cell proliferation.

Example 4

Figure 3:
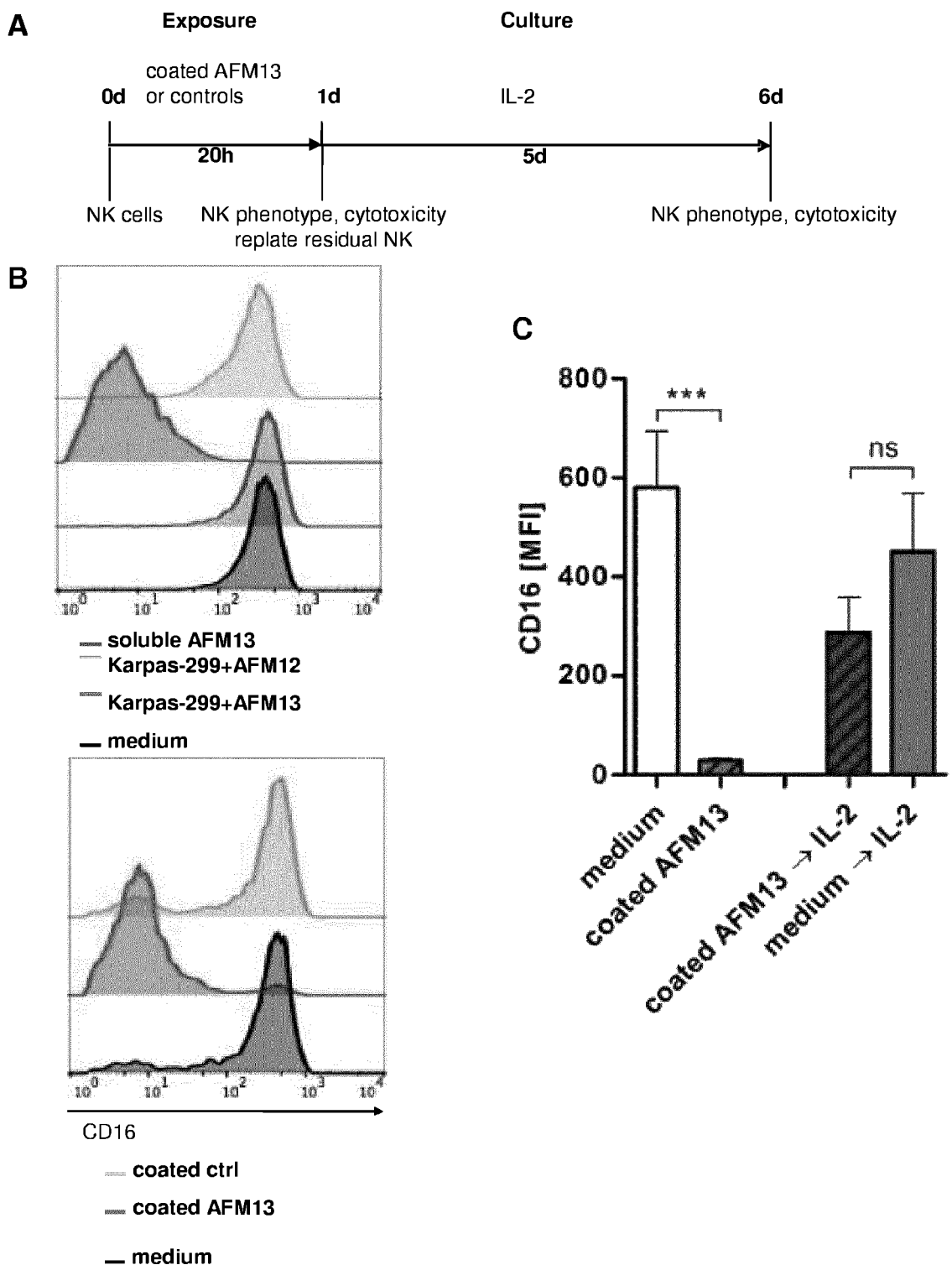
FIG. 3 shows recovery of NK cell cytotoxicity after transient dysfunction subsequent to AFM13 exposure:
A. Scheme of the experimental setup. B. CD16 expression was measured on NK cells after 20-hour co-culture with Karpas-299 cells with AFM13, or after culture on coated AFM13 (or controls as in FIG. 2, B); representative histograms of six experiments. C. CD16 expression on NK cells (a) after exposure to coated AFM13 or (b) medium, or on NK cells after culture in IL-2 (400 U/mL) for five days subsequent to exposure to coated AFM13 or (d) without pre-exposure (IL-2 only); MFI data of nine experiments. D. lysis of and E degranulation to AFM13-opsonized Karpas-299 cells by NK cells that had been cultured as described in C; cumulative data (E:T 2.5:1) of two to five experiments. F. natural lysis of and G. degranulation to K562 cells by NK cells that had been cultured as described in C; cumulative data (E:T 2.5:1) of two to six experiments.
Figure 3:
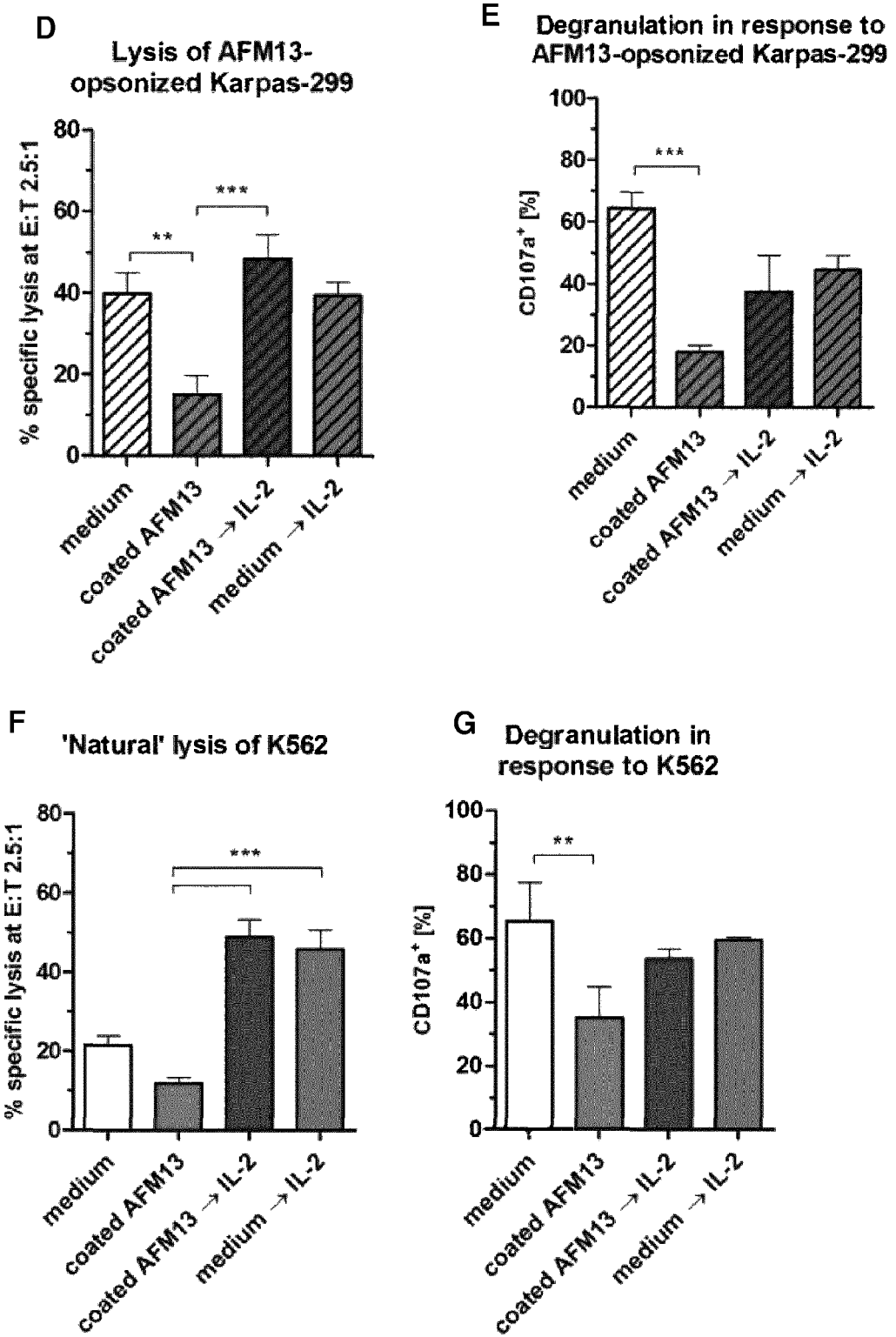

Recovery of CD16A-Mediated NK Cell Function after CD30/CD16A Tandem Diabody (AFM13) Exposure Concomitant with the induction of activation markers, we observed an almost complete loss of CD16 expression on NK cells after 20-hour culture with AFM13-opsonized target cells or coated AFM13 (FIG. 3, A-C). Importantly, this effect was transient, since CD16 expression could be restored when the NK cells were replated after AFM13 tandem diabody exposure and subsequently cultured in low or high doses of IL-2 or IL-15 for 5 days (FIG. 3, C). CD16 down-regulation as observed by flow cytometry was not due to epitope masking, since the detection of CD16 by anti-CD16 3G8 was not altered in the presence of AFM13. Instead, CD16 down-regulation relied at least in part on metalloproteinase-mediated cleavage as previously reported for CD16 down-regulation by anti-CD16 3G8, rituximab and BiKEs (Borrego, et al., 1994, Mota, et al., 2004, Romee, et al., 2013, Wiernik, et al., 2013).

Figure 4:
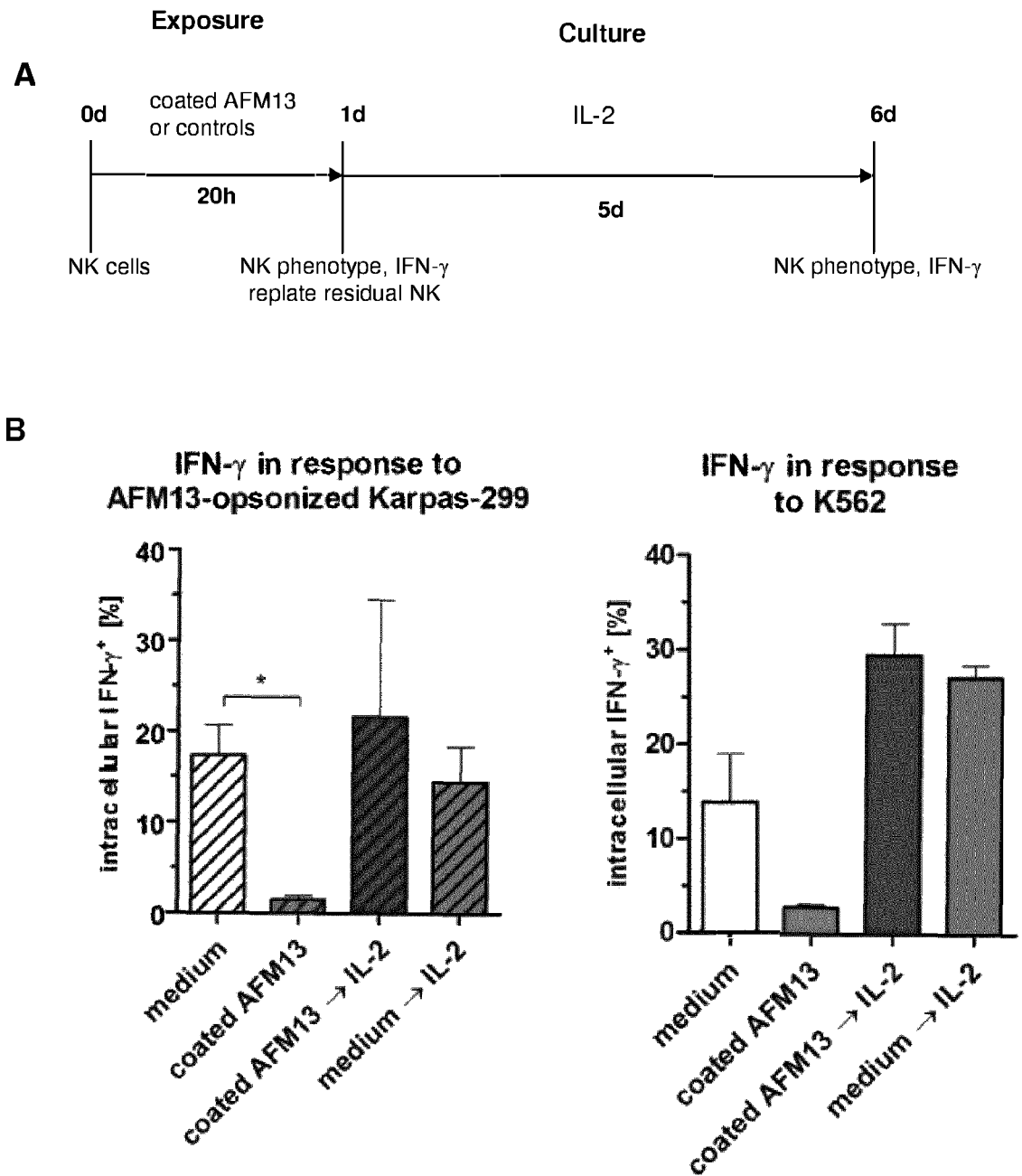
FIG. 4 shows recovery of NK cell IFN-γ after transient selective dysfunction subsequent to CD30/CD16A tandem diabody exposure:
Intracellular IFN-γ expression in response to A. AFM13-opsonized Karpas-299 cells, B. K562 cells and C. IL-12/15/18 by NK cells that had been cultured as described in FIG. 3, C; cumulative data of two to four experiments. D. Expression of the high-affinity IL-12Rβ and IL-18Rα on NK cells previously activated by coated AFM13 or cultured in medium (left pair of histograms); and by NK cells cultured in IL-2 for 5 days subsequent to AFM13 exposure or in IL-2 without pre-exposure (right pair of histograms); representative data for four experiments.
Figure 4:
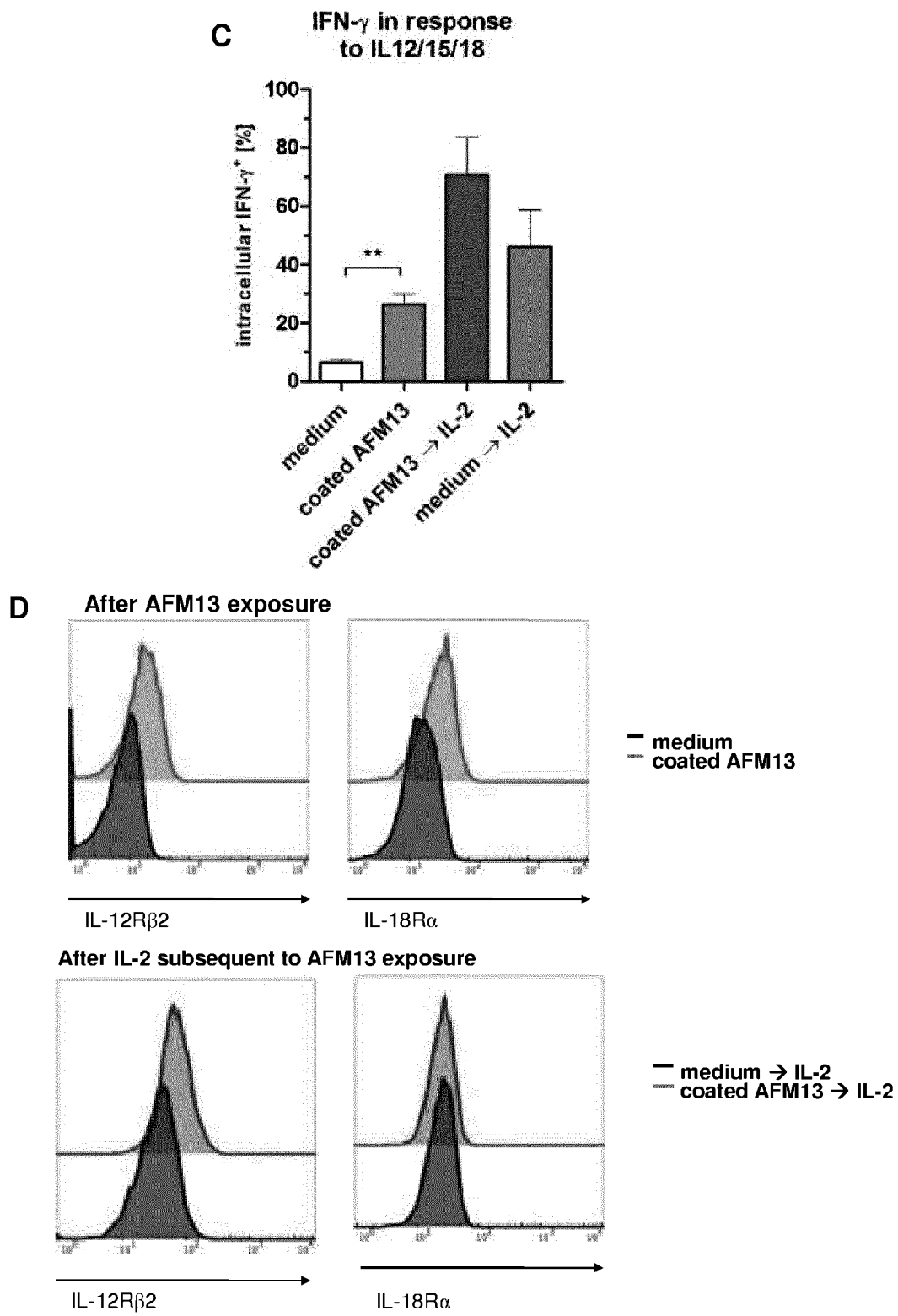

Next, the transient reduction in CD16 after AFM13 tandem diabody exposure affected NK cell cytotoxicity was tested in a subsequent second exposure. Indeed, subsequent to a co-culture with L428 cells in the presence of AFM13 tandem diabody, lysis of a new round of AFM13-opsonized target cells (second exposure) was impaired compared to lysis by previously non-co-cultured NK cells. NK cell cytotoxicity remained unaltered after a co-culture with L428 cells in the presence of AFM12 tandem diabody. To dissect this impaired cytotoxic function in a tumor cell-free system, NK cell cytotoxicity was assessed after exposure to coated AFM13 tandem diabody. NK cell cytotoxicity, degranulation and intracellular IFN-γ expression in response to AFM13-opsonized Karpas-299 cells and was significantly reduced after 20-hour culture on coated AFM13 tandem diabody, despite intact perforin and granzyme B levels (FIG. 3, D-E; FIG. 4, A). Likewise, lysis of AFM13-opsonized L428 and AFM12-opsonized Daudi cells was impaired (Figure S4, C). Still, the residual AFM13-mediated lysis was higher than lysis of non-opsonized tumor cells. Importantly, the reduced NK cell cytotoxicity after AFM13 tandem diabody exposure could be fully restored after subsequent culture in IL-2 or IL-15 for 5 days (FIG. 3, D). Similarly, coated rituximab impaired CD16 expression and NK cell cytotoxicity that could be restored after culture in IL-2.

The maximal level of degranulation and intracellular IFN-γ expression inducible by PMA/ionomycin was also decreased after exposure to AFM13 tandem diabody, suggesting a broader dysfunction. In fact, also CD16A-independent 'natural' NK cell cytotoxicity, degranulation and intracellular IFN-γ expression in response to the prototypical target cell line K562 as well as HuT-78 cells was disturbed after AFM13 tandem diabody exposure. (FIG. 3, F; FIG. 4, B). This inhibition could be reverted by a subsequent culture in IL-2 for five days. Notably, IFN-γ expression in response to IL-12/15/18 remained intact and was moderately increased after AFM13 tandem diabody exposure, which coincided with increased expression of the high-affinity IL-12Rβ2 and IL-18Rα receptors (FIG. 4, C-D). Thus, AFM13-pre-activated NK cells appeared to be more sensitive to not only IL-2 and IL-15 but also IL-12 and IL-18.

Hence, while NK cell functionality was enhanced in direct response to AFM13-opsonized target cells, AFM13 tandem diabody exposure subsequently led to a selective transient dysfunction towards a second exposure to tumor cells, which could be rescued by IL-2 or IL-15 stimulation.

Figure 6:
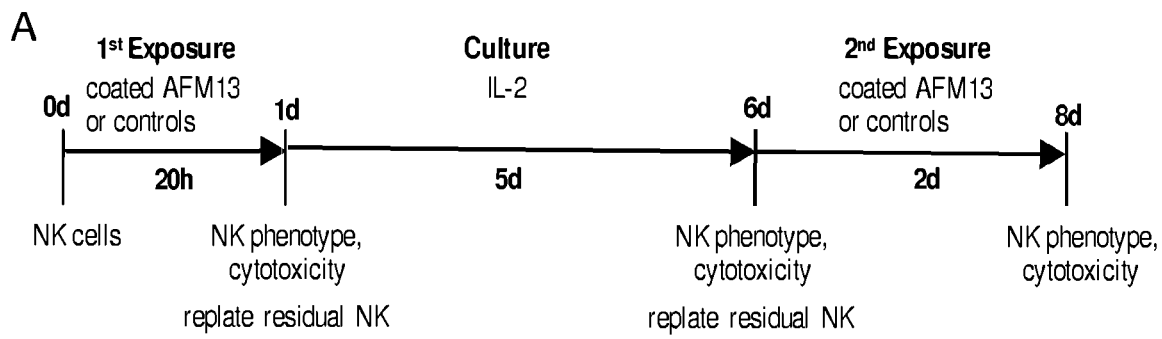
FIG. 6 shows transient reduction in target cell killing capacity of NK cells after repeated exposure to AFM13 despite cytokine stimulation:
A. Scheme of the experimental setup: $1^{st}$ exposure to coated AFM13 for 20 h, subsequent culture in IL-2 (400 U/mL) for five days and $2^{nd}$ exposure to coated AFM13 for additional 2 days B. Lysis of AFM13-opsonized Karpas-299 cells by NK cells that had been cultured as described in A; (E:T 2.5:1).
Figure 6:
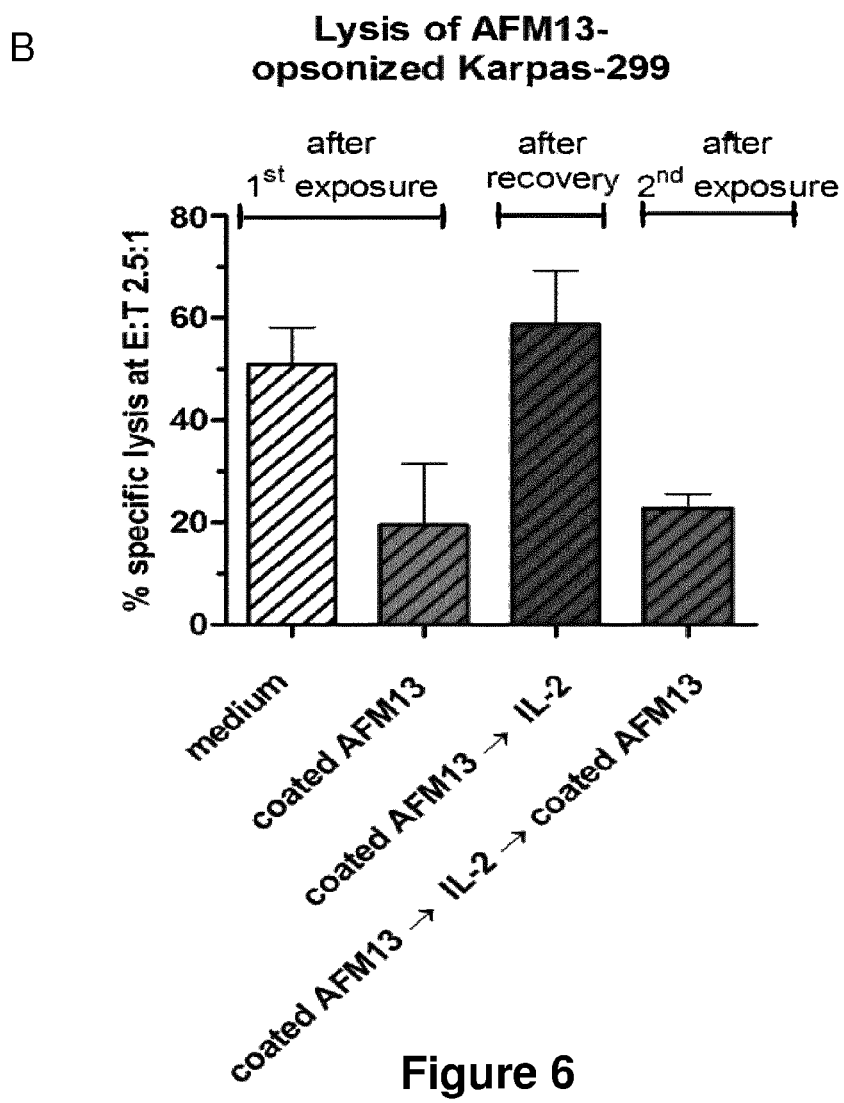

FIG. 6 shows that after cytokine recovery of the NK cells' cytotoxic potential, a second exposure to AFM13 impairs NK cell cytotoxicity again. The reduction in cytotoxic potency after the $2^{nd}$ exposure to AFM13 is comparable with that after the 1st exposure. This data shows that in the presence of AFM13, cytokine stimulation cannot (at least not completely) revert the transient loss of NK cells' potency induced by AFM13. Thus, for efficient cytokine-stimulated recovery of NK cells' cytotoxicity it is important that the concentration of the anti-CD16A antigen binding protein is kept low or absent during the recovery phase.

Example 5

Figure 5:
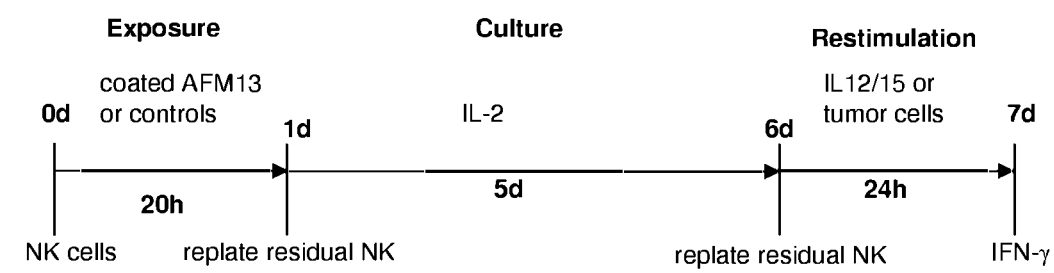
FIG. 5 shows that pre-activation by a CD30/CD16A tandem diabody primes NK cell memory-like IFN-γ production and cytotoxicity:
A. IFN-γ production in response to 24-hour re-stimulation by IL-12/15, K562, L428 by NK cells cultured in IL-2 for 5 days subsequent to the exposure to coated AFM13, or cultured only in IL-2 without pre-exposure; cumulative data of five experiments. B. Lysis of non-opsonized CD30⁺ Karpas-299 and HDLM-2 cells as well as CD30⁺ Daudi and CD30⁺ L1236 cells by freshly-isolated NK cells, or by NK cells cultured in IL-2 for 5 days subsequent to the exposure to coated AFM13, or cultured only in IL-2 without pre-exposure; cumulative data of two to six experiments.
Figure 5:
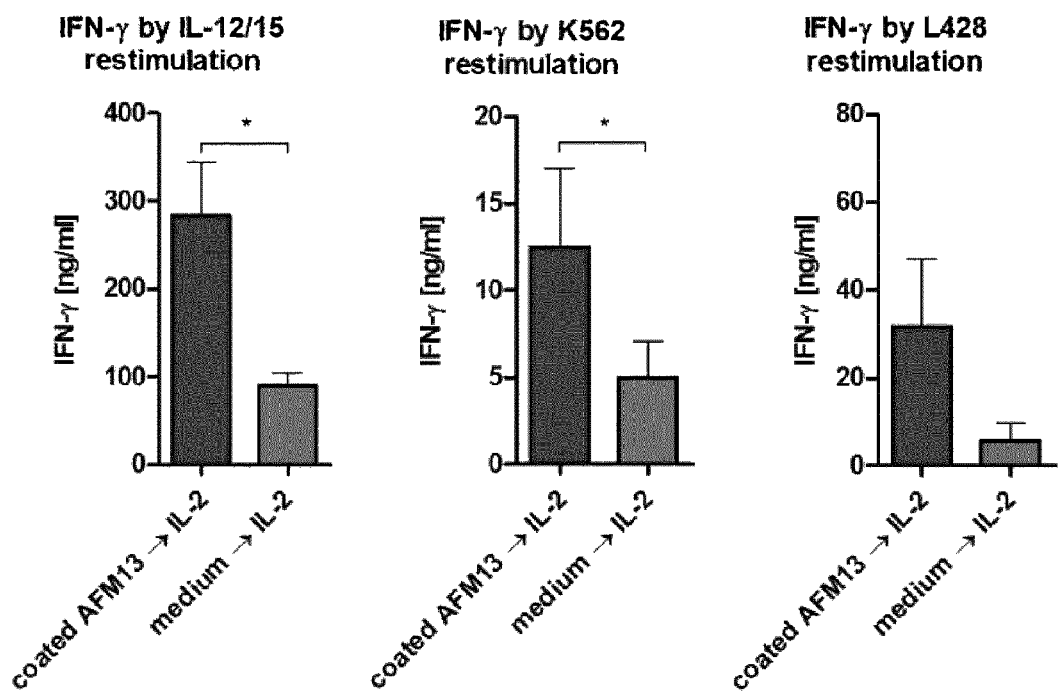
Figure 5:
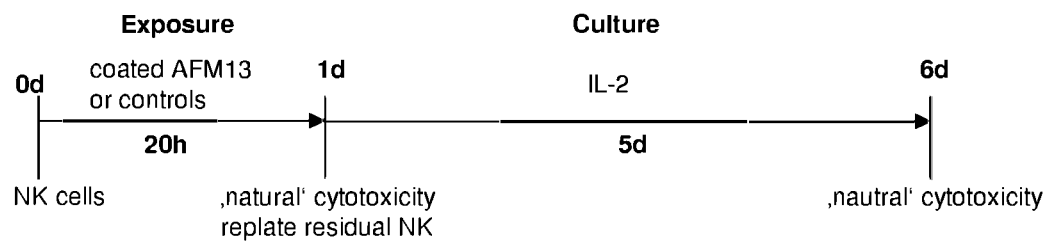
Figure 5:
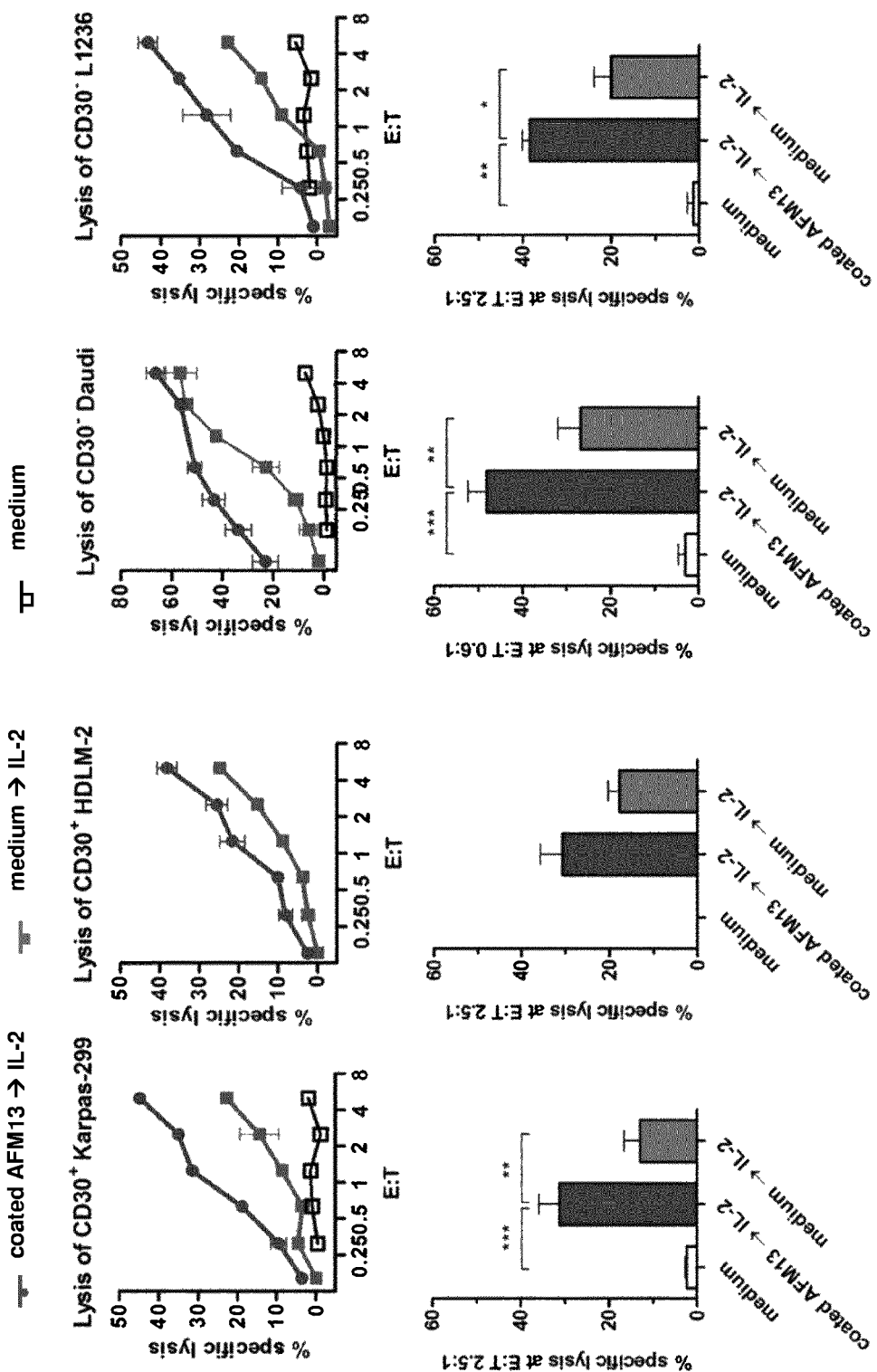

CD30/CD16A Tandem Diabody (AFM13)-Pre-Activation Through CD16A Primes Potent NK Cell IFN-γ Production It was determined whether pre-activation by AFM13 tandem diabody could modulate IFN-γ production of IL-2-cultured NK cells when restimulated in the absence of AFM13 tandem diabody. In response to IL-12/15, IFN-γ production was significantly improved when IL-2-cultured NK cells had initially been exposed to AFM13 (FIG. 5, A). More strikingly, IFN-γ production was additionally amplified in response to restimulation by K562 or L428 cells (FIG. 5, A), indicating that the pre-activation by AFM13 tandem diabody amplified the IFN-γ response to cytokines and lymphoma cells.

CD30/CD16A Tandem Diabody (AFM13)-Pre-Activation Through CD16A Primes the Lysis of $CD30^+$ and Even $CD30^+$ Lymphoma Cells It is shown that a culture in IL-2 subsequent to AFM13 tandem diabody exposure fully restored NK cell cytotoxicity (FIG. 3, D+F). Hence, AFM13-experienced NK cells were equally potent in response to a second exposure to AFM13-opsonized target than NK cells cultured in IL-2 alone. In a next step, it was explored whether pre-activation by AFM13 tandem diabody could affect the 'natural' lysis in response to a second exposure to (non-opsonized) $CD30^+$ or $CD30^+$ lymphoma cells almost resistant to 5-day IL-2-cultured NK cells. Remarkably, lysis of $CD30^+$ Karpas-299 and HDLM-2 cells was amplified when IL-2 or IL-15-cultured NK cells had initially been exposed to AFM13; these cells were resistant to naïve NK cells and almost resistant to IL-2 or IL-15-cultured NK cells (FIG. 5, B. More importantly, even the lysis of the $CD30^+$ lymphoma cell lines L1236 and Daudi was amplified by the initial AFM13 tandem diabody exposure (FIG. 5, B). This amplification was particularly evident for target cells weakly susceptible to IL-2-cultured NK cells, while the strong lysis of sensitive K562 target cells by IL-2-cultured NK cells was not further improved. The enhanced cytotoxic function was also observed for AFM12 tandem diabody or rituximab-pre-activated NK cells.

Thus, AFM13-experienced cytokine-activated NK cells exhibited amplified cytotoxicity in response to $CD30^+$ and even $CD30^+$ lymphoma cells relative to NK cells only activated by cytokines.

Example 6

Recovery of CD16A-Mediated NK Cell Function after Exposure to EGFR/CD16A (AFM24) Tandem Diabody and BCMAxCD16A (AFM26) Tandem Diabody.

Figure 7:
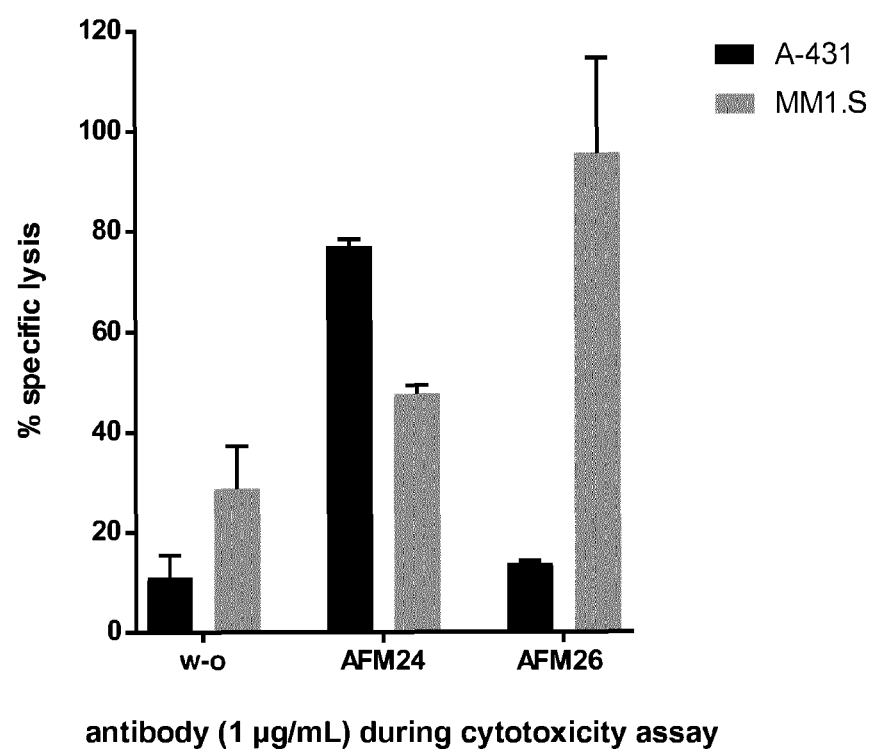
FIG. 7 shows that EGFR/CD16A tandem diabody (AFM24) and BCMA/CD16A tandem diabody (AFM26) induce a functional activation of NK cells in response to EGFR⁺ and BCMA⁺ target cells, respectively. The cytotoxic activity of NK cells in the presence of AFM24 (EGFR/CD16A tandem diabody) and AFM26 (BCMA/CD16A tandem diabody) on EGFR⁺ A-431 and BCMA⁺ MM.1S target cells is shown. 4h calcein-release with O/N-cultured NK cells as effector cells at an E:T ratio of 2.5:1. N=2 independent experiments.

Similarly as for AFM13 shown in Example 2, EGFR/CD16A tandem diabody and BCMA/CD16A tandem diabody induce a functional activation of NK cells in response to $EGFR^+$ and $BCMA^+$ target cells, respectively (FIG. 7).

Figure 8:
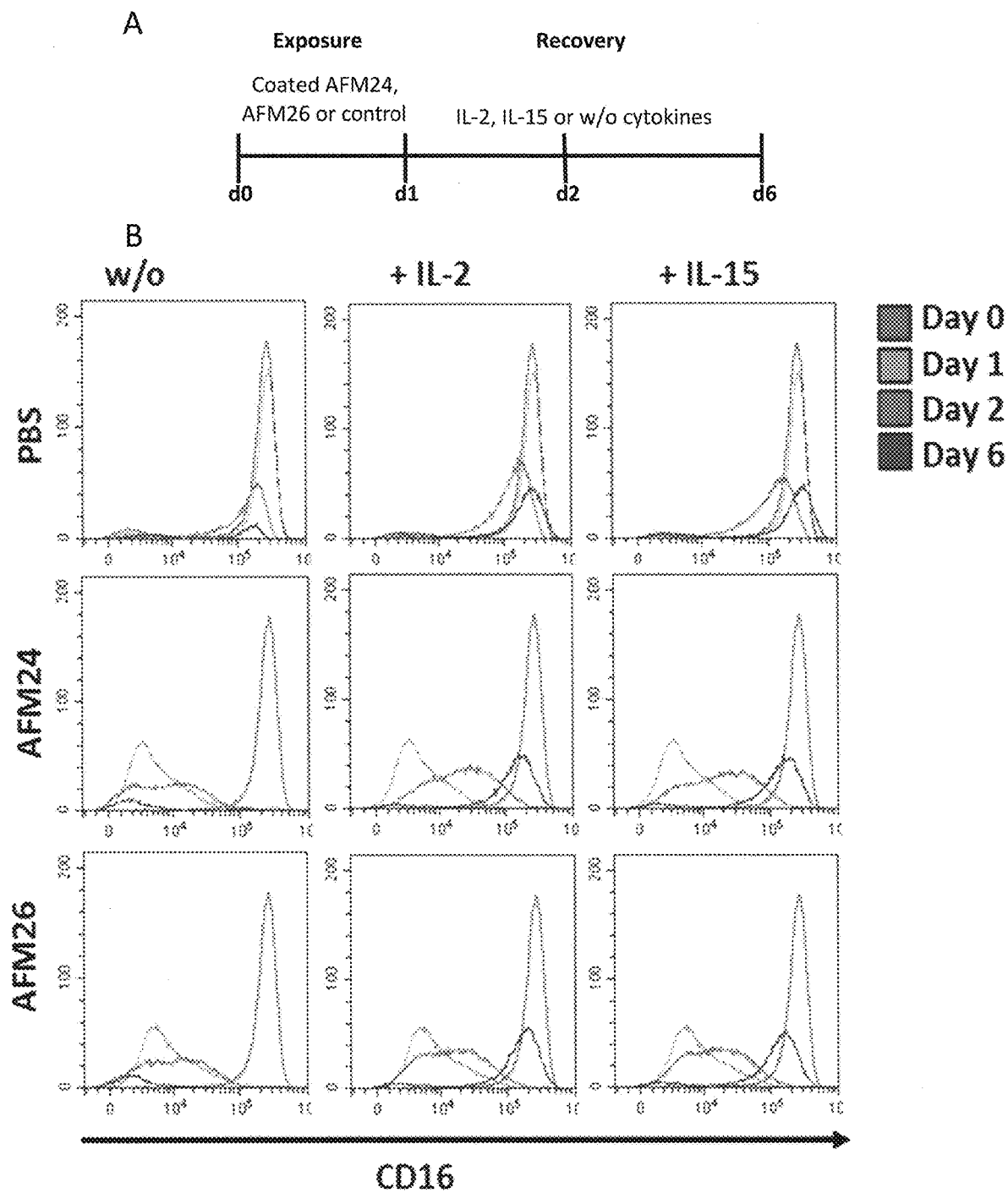
FIG. 8 shows recovery of CD16A-mediated NK cell function after exposure to AFM24 (EGFR/CD16A tandem diabody) and AFM26 (BCMA/CD16A tandem diabody), respectively.
A. Experimental scheme for assessing the phenotypic and functional NK cell recovery following exposure to AFM24 and AFM26 respectively. B. Flow cytometric analysis of CD16 on the NK cell surface upon 24 hr exposure to PBS or 10 µg/mL coated AFM24 and AFM26, respectively. The cell surface expression of CD16 in absence and presence of the indicated cytokines during the recovery phase (day 1 to day 6) is shown. NK cells were identified as CD45⁺ CD56⁺ viable cells in flow cytometry. C. Quantification of the CD16 expression on the NK cell surface upon exposure to plate-bound AFM24 and AFM26. N=2 independent experiments. D. Assessment of the specific cytotoxic NK cell function in presence of AFM24 target cells A-431 and AFM26 target cells MM.1S at an E:T ratio of 2.5:1. The respective tandem diabody was supplemented to the applied 4 h calcein-release assay (c=1 µg/mL). The NK cells were treated with 400U/mL IL-2 if indicated. N=2 independent experiments.
Figure 8:
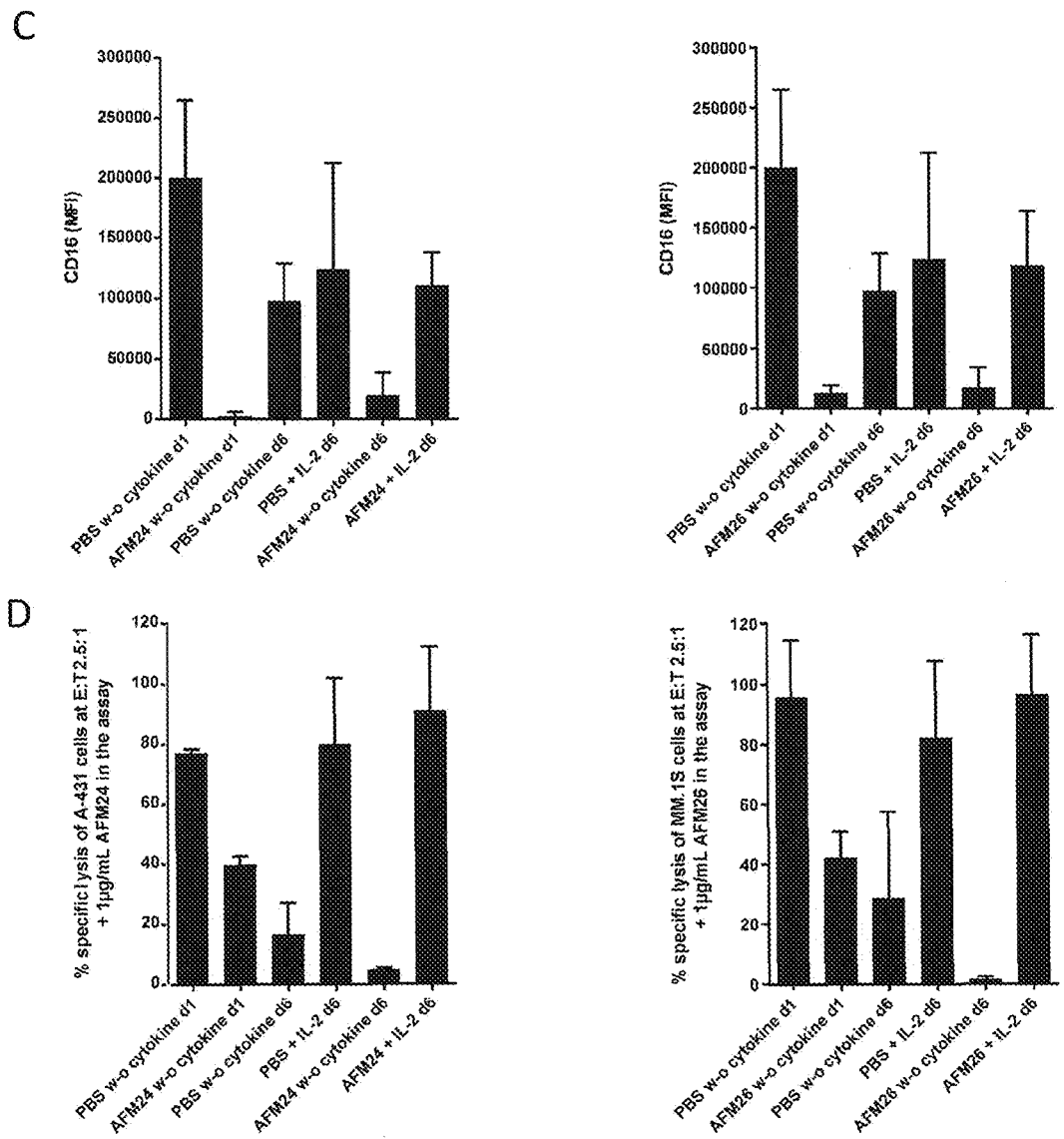
Figure 9:
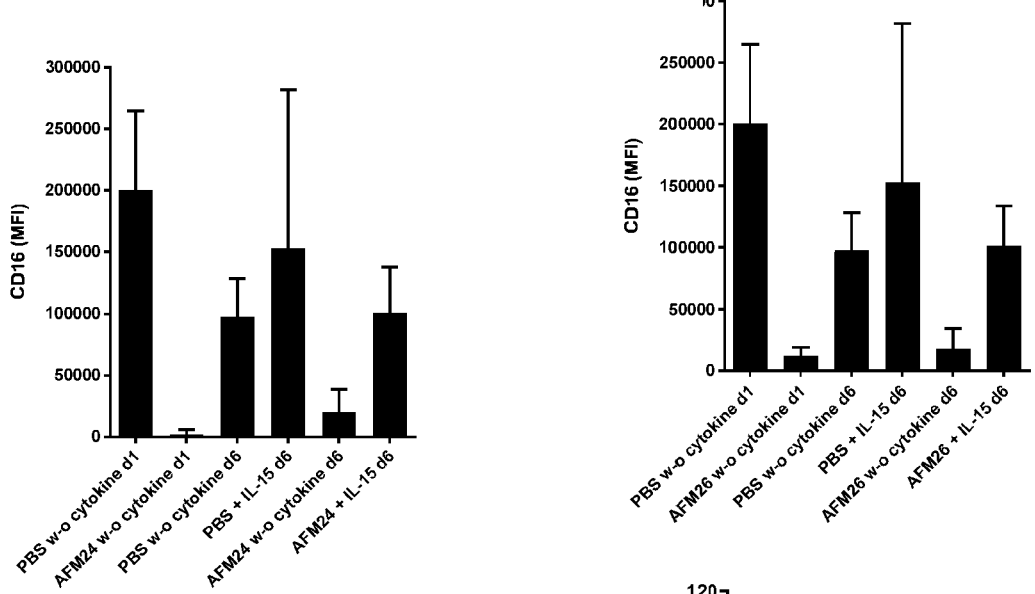
FIG. 9 shows recovery of CD16A-mediated NK cell function after exposure to AFM24 (EGFR/CD16A) and AFM26 (BCMA/CD16A) respectively.
A. Quantification of the CD16 expression on the NK cell surface upon exposure to AFM24 and AFM26. N=2 independent experiments. B. Assessment of the specific cytotoxic NK cell function in presence of AFM24 target cells A-431 and AFM26 target cells MM.1S at an E:T ratio of 2.5:1. The respective tandem diabody was supplemented to the applied 4 h calcein-release assay (c=1 µg/mL). The NK cells were treated with 10 ng/mL IL-15 if indicated. N=2 independent experiments.
Figure 9:
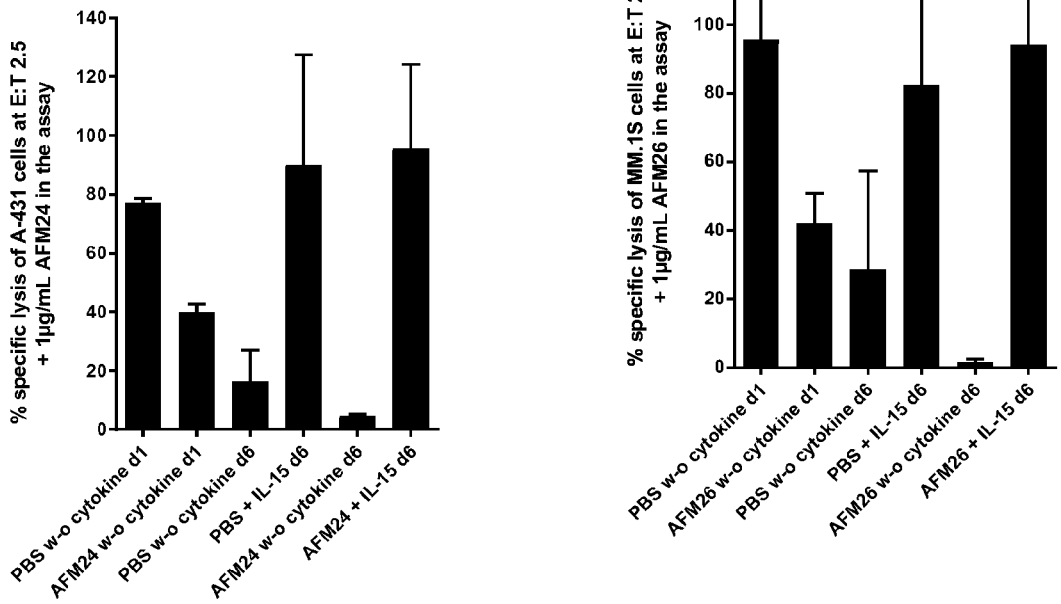

Similarly as shown for AFM13 in Example 4, recovery of CD16 expression and CD16A-mediated NK cell function is achieved by treatment with IL-2 or IL-15 for 5 days after exposure to EGFR/CD16A tandem diabody and BCMA/CD16A tandem diabody, respectively, as it is described in Example 4 (FIGS. 8 and 9).

Therefore, the intermittent dosage regimen described herein can be employed for multispecific, i.e. bispecific, CD16A antigen binding proteins independent from the target antigen domain.

| Sequence Summary: | |
|---|---|
| SEQ NO. | Sequence |
| 1 | HCDR1 CD16A<br>GYTFTSYY |

-continued

Sequence Summary:

| SEQ NO. | Sequence |
|---|---|
| 2 | HCDR2 CD16A<br>IEPMYGST |
| 3 | HCDR3 CD16A<br>ARGSAYYYDFADY |
| 4 | LCDR1 CD16A<br>NIGSKN |
| 5 | LCDR2 CD16A<br>QDN |
| 6 | LCDR3 CD16A<br>QVWDNYSVL |
| 7 | HCDR2 CD16A<br>INPSGGST |
| 8 | VH CD16A<br>QVQLVQSGAEVKKPGESLKVSCKASGYTFTSYYMHWVRQAPGQ<br>GLEWMGAIEPMYGSTSYAQKFQGRVTMTRDTSTSTVYMELSSL<br>RSEDTAVYYCARGSAYYYDFADYWGQGTLVTVSS |
| 9 | VL CD16A<br>SYVLTQPSSVSVAPGQTATISCGGHNIGSKNVHWYQQRPGQSP<br>VLVIYQDNKRPSGIPERFSGSNSGNTATLTISGTQAMDEADYY<br>CQVWDNYSVLFGGGTKLTVL |
| 10 | VH CD16A<br>QVQLVQSGAEVKKPGESLKVSCKASGYTFTSYYMHWVRQAPGQ<br>GLEWMGIINPSGGSTSYAQKFQGRVTMTRDTSTSTVYMELSSL<br>RSEDTAVYYCARGSAYYYDFADYWGQGTLVTVSS |

REFERENCES

Bibeau, F., Lopez-Crapez, E., Di, F. F., Thezenas, S., Ychou, M., Blanchard, F., Lamy, A., Penault-Llorca, F., Frebourg, T., Michel, P., Sabourin, J. C., Boissiere-Michot, F. 2009. Impact of Fc{gamma}RIIa-Fc{gamma}RIIIa polymorphisms and KRAS mutations on the clinical outcome of patients with metastatic colorectal cancer treated with cetuximab plus irinotecan. J. Clin. Oncol. 27, 1122-1129.

Bonnema, J. D., Karnitz, L. M., Schoon, R. A., Abraham, R. T., Leibson, P. J. 1994. Fc receptor stimulation of phosphatidylinositol 3-kinase in natural killer cells is associated with protein kinase C-independent granule release and cell-mediated cytotoxicity. J Exp Med 180, 1427-1435.

Borrego, F., Lopez-Beltran, A., Pena, J., Solana, R. 1994. Downregulation of Fc gamma receptor IIIA alpha (CD16-II) on natural killer cells induced by anti-CD16 mAb is independent of protein tyrosine kinases and protein kinase C. Cell Immunol 158, 208-217.

Brandt, C. S., Baratin, M., Yi, E. C., Kennedy, J., Gao, Z., Fox, B., Haldeman, B., Ostrander, C. D., Kaifu, T., Chabannon, C., Moretta, A., West, R., Xu, W., Vivier, E., Levin, S. D. 2009. The B7 family member B7-H6 is a tumor cell ligand for the activating natural killer cell receptor NKp30 in humans. J Exp Med 206, 1495-1503.

Bryceson, Y. T., Ljunggren, H. G., Long, E. O. 2009. Minimal requirement for induction of natural cytotoxicity and intersection of activation signals by inhibitory receptors. Blood 114, 2657-2666.

Bryceson, Y. T., March, M. E., Ljunggren, H. G., Long, E. O. 2006. Synergy among receptors on resting NK cells for the activation of natural cytotoxicity and cytokine secretion. Blood 107, 159-166.

Capuano, C., Romanelli, M., Pighi, C., Cimino, G., Rago, A., Molfetta, R., Paolini, R., Santoni, A., Galandrini, R. 2015. Anti-CD20 Therapy Acts via FcgammaRIIIA to Diminish Responsiveness of Human Natural Killer Cells. Cancer Res 75, 4097-4108.

Cassatella, M. A., Anegon, I., Cuturi, M. C., Griskey, P., Trinchieri, G., Perussia, B. 1989. Fc gamma R(CD16) interaction with ligand induces Ca2+ mobilization and phosphoinositide turnover in human natural killer cells. Role of Ca2+ in Fc gamma R(CD16)-induced transcription and expression of lymphokine genes. J Exp Med 169, 549-567.

Cerwenka, A., Lanier, L. L. 2001. Natural killer cells, viruses and cancer. Nat. Rev. Immunol. 1, 41-49.

Cerwenka, A., Lanier, L. L. 2016. Natural killer cell memory in infection, inflammation and cancer. Nat Rev Immunol 16, 112-123.

Charych D., Khalili, S., Dixit, V., Kirk, P., Chang, T., Langowski, J., Rubas, W., Doberstein, K., Eldon, M., Hoch, U., Zalevsky, J., 2017, Modeling the receptor pharmacology, pharmacokinetics, and pharmacodynamics of NKTR-214, a kinetically-controlled interleukin-2 (IL2) receptor agonsit for cancer immunotherapy, PLos ONE 12(7):e0179431.

Chatila, T., Silverman, L., Miller, R., Geha, R. 1989. Mechanisms of T cell activation by the calcium ionophore ionomycin. J Immunol 143, 1283-1289.

Cooper, M. A., Elliott, J. M., Keyel, P. A., Yang, L., Carrero, J. A., Yokoyama, W. M. 2009. Cytokine-induced memory-like natural killer cells. Proc Natl Acad Sci USA 106, 1915-1919.

Dall'Ozzo, S., Tartas, S., Paintaud, G., Cartron, G., Colombat, P., Bardos, P., Watier, H., Thibault, G. 2004. Rituximab-dependent cytotoxicity by natural killer cells: influence of FCGR3A polymorphism on the concentration-effect relationship. Cancer Res 64, 4664-4669.

de Landazuri, M. O., Silva, A., Alvarez, J., Herberman, R. B. 1979. Evidence that natural cytotoxicity and antibody-dependent cellular cytotoxicity are mediated in humans by the same effector cell populations. J Immunol 123, 252-258.

Galandrini, R., Tassi, I., Mattia, G., *Lenti*, L., Piccoli, M., Frati, L., Santoni, A. 2002. SH2-containing inositol phosphatase (SHIP-1) transiently translocates to raft domains and modulates CD16-mediated cytotoxicity in human NK cells. Blood 100, 4581-4589.

Gasser, S., Raulet, D. H. 2006. Activation and self-tolerance of natural killer cells. Immunol Rev 214, 130-142.

Gasteiger, G., Hemmers, S., Firth, M. A., Le Floc'h, A., Huse, M., Sun, J. C., Rudensky, A. Y. 2013. IL-2-dependent tuning of NK cell sensitivity for target cells is controlled by regulatory T cells. J Exp Med 210, 1167-1178.

Hara, H., Ishihara, C., Takeuchi, A., Xue, L., Morris, S. W., Penninger, J. M., Yoshida, H., Saito, T. 2008. Cell type-specific regulation of ITAM-mediated NF-kappaB activation by the adaptors, CARMA1 and CARDS. J Immunol 181, 918-930.

Harris, M. 2004. Monoclonal antibodies as therapeutic agents for cancer. Lancet Oncol 5, 292-302. Kim, M., Kim, T. J., Kim, H. M., Doh, J., Lee, K. M. 2017.

Multi-cellular natural killer (NK) cell clusters enhance NK cell activation through localizing IL-2 within the cluster. Sci Rep 7, 40623.

Kipriyanov SM: Methods Mol Biol 2003; 207:323-33

Kipriyanov SM: Methods Mol. Biol. 2009; 562:177-93

Koch, J., Steinle, A., Watzl, C., Mandelboim, O., 2013, Activating natural cytotoxicity receptors of natural killer cells in cancer and infection, Trends. Immunol., 34(4): 192-91

Koehl, U., Kalberer, C., Spanholtz, J., Lee, D. A., Miller, J. S., Cooley, S., Lowdell, M., Uharek, L., Klingemann, H., Curti, A., Leung, W. and Alici, E., 2016, Advances in clinical NK cel studies:Donor selection, manufacturing and quality control, Oncoimmunology, 5(4) e1115178.

Kondadasula, S. V., Roda, J. M., Parihar, R., Yu, J., Lehman, A., Caligiuri, M. A., Tridandapani, S., Burry, R. W., Carson, W. E., 3rd. 2008. Colocalization of the IL-12 receptor and FcgammaRIIIa to natural killer cell lipid rafts leads to activation of ERK and enhanced production of interferon-gamma. Blood 111, 4173-4183.

Kontermann, R. E. Brinkmann, U. The making of bispecific antibodies, 2017 mAbs, 9(2):182-212).

Kufe D W, Pollock R E, Weichselbaum RR. et al. 2003, Categories of Tumor Antigens, Holland-Frei Cancer Medicine. 6th edition., editors Hamilton (ON):Becker Kuylenstierna, C., Bjorkstrom, N. K., Andersson, S. K., Sahlstrom, P., Bosnjak, L., Paquin-Proulx, D., Malmberg, K. J., Ljunggren, H. G., Moll, M., Sandberg, J. K. 2011. NKG2D performs two functions in invariant NKT cells: direct TCR-independent activation of NK-like cytolysis and co-stimulation of activation by CD1d. Eur J Immunol 41, 1913-1923.

Lajoie, L., Congy-Jolivet, N., Bolzec, A., Gouilleux-Gruart, V., Sicard, E., Sung, H. C., Peiretti, F., Moreau, T., Vie, H., Clemenceau, B., Thibault, G. 2014. ADAM17-mediated shedding of FcgammaRIIIA on human NK cells: identification of the cleavage site and relationship with activation. J Immunol 192, 741-751.

Lanier, L. L., Ruitenberg, J. J., Phillips, J. H. 1988. Functional and biochemical analysis of CD16 antigen on natural killer cells and granulocytes. J Immunol 141, 3478-3485.

Li, W., Yang, H., Dimitrov, D. S. 2016. Identification of high-affinity anti-CD16A allotype-independent human antibody domains. Exp Mol Pathol 101, 281-289.

Liu, B., Kong, L., Han K., Hong, H, Marcus, W. D., Chen, X.,

Leng, E. K., Alter, S., Zhu, X., Rubinsein M. R., Shi, S., Rhode, P.r., Cai, W. Wong, H. C.; 2016 A novel fusion of ALT-803 (interleukin (IL)-15 superagonist) with an antibody demonstrates antigen-specific antitumor responses, Journal of Biological Chemistry, vol. 291 (46), pp. 23869-23881

Lissoni P, Barni S, Ardizzoia A, Olivini G, Brivio F, Tisi E, Tancini G, Characiejus D, Kothari L. 1993 Cancer immunotherapy with low-dose interleukin-2 subcutaneous administration: potential efficacy in most solid tumor histotypes by a concomitant treatment with the pineal hormone melatonin. J Biol Regul Homeost Agents. 1993 October-December; 7(4):121-5

Luetke-Eversloh, M., Hammer, Q., Durek, P., Nordstrom, K., Gasparoni, G., Pink, M., Hamann, A., Walter, J., Chang, H. D., Dong, J., Romagnani, C. 2014. Human cytomegalovirus drives epigenetic imprinting of the IFNG locus in NKG2Chi natural killer cells. PLoS Pathog 10, e1004441.

Marquez, M. E., Millet, C., Stekman, H., Conesa, A., Deglesne, P. A., Toro, F., Sanctis, J. D., Blanca, I. 2010. CD16 cross-linking induces increased expression of CD56 and production of IL-12 in peripheral NK cells. Cell Immunol 264, 86-92.

Moretta, L., Bottino, C., Pende, D., Castriconi, R., Mingari, M. C., Moretta, A. 2006. Surface NK receptors and their ligands on tumor cells. Semin Immunol 18, 151-158.

Mota, G., Moldovan, I., Calugaru, A., Hirt, M., Kozma, E., Galatiuc, C., Brasoveanu, L., Boltz-Nitulescu, G. 2004. Interaction of human immunoglobulin G with CD16 on natural killer cells: ligand clearance, FcgammaRIIIA turnover and effects of metalloproteinases on FcgammaRIIIA-mediated binding, signal transduction and killing. Scand J Immunol 59, 278-284.

Musolino, A., Naldi, N., Bortesi, B., Pezzuolo, D., Capelletti, M., Missale, G., Laccabue, D., Zerbini, A., Camisa, R., Bisagni, G., Neri, T. M., Ardizzoni, A. 2008. Immunoglobulin G fragment C receptor polymorphisms and clinical efficacy of trastuzumab-based therapy in patients with HER-2/neu-positive metastatic breast cancer. J. Clin. Oncol. 26, 1789-1796.

Nakahira, M., Ahn, H. J., Park, W. R., Gao, P., Tomura, M., Park, C. S., Hamaoka, T., Ohta, T., Kurimoto, M., Fujiwara, H. 2002. Synergy of IL-12 and IL-18 for IFN-gamma gene expression: IL-12-induced STAT4 contributes to IFN-gamma promoter activation by up-regulating the binding activity of IL-18-induced activator protein 1. J Immunol 168, 1146-1153.

Ni, J., Holsken, O., Miller, M., Hammer, Q., Luetke-Eversloh, M., Romagnani, C., Cerwenka, A. 2016. Adoptively transferred natural killer cells maintain long-term antitumor activity by epigenetic imprinting and CD4+ T cell help. Oncoimmunology 5, e1219009.

Ni, J., Miller, M., Stojanovic, A., Garbi, N., Cerwenka, A. 2012. Sustained effector function of IL-12/15/18-preactivated NK cells against established tumors. J. Exp. Med. 209, 2351-2365.

Pahl, J., Cerwenka, A. 2017. Tricking the balance: NK cells in anti-cancer immunity. Immunobiology 222, 11-20.

Pahl, J. H., Ruslan, S. E., Buddingh, E. P., Santos, S. J., Szuhai, K., Serra, M., Gelderblom, H., Hogendoorn, P. C., Egeler, R. M., Schilham, M. W., Lankester, A. C. 2012. Anti-EGFR antibody cetuximab enhances the cytolytic activity of natural killer cells toward osteosarcoma. Clin Cancer Res 18, 432-441.

Parkhurst, M. R., Riley, J. P., Dudley, M. E., Rosenberg, S. A. 2011. Adoptive transfer of autologous natural killer cells leads to high levels of circulating natural killer cells but does not mediate tumor regression. Clin Cancer Res 17, 6287-6297.

Reiners, K. S., Kessler, J., Sauer, M., Rothe, A., Hansen, H. P., Reusch, U., Hucke, C., Kohl, U., Durkop, H., Engert, A., von Strandmann, E. P. 2013. Rescue of impaired NK cell activity in hodgkin lymphoma with bispecific antibodies in vitro and in patients. Mol Ther 21, 895-903.

Reusch, U., Burkhardt, C., Fucek, I., Le Gall, F., Le Gall, M., Hoffmann, K., Knackmuss, S. H., Kiprijanov, S., Little, M., Zhukovsky, E. A. 2014. A novel tetravalent bispecific TandAb (CD30/CD16A) efficiently recruits NK cells for the lysis of CD30+ tumor cells. MAbs 6, 728-739.

Rolle, A., Brodin, P. 2016. Immune Adaptation to Environmental Influence: The Case of NK Cells and HCMV. Trends Immunol 37, 233-243.

Romee, R., Foley, B., Lenvik, T., Wang, Y., Zhang, B., Ankarlo, D., Luo, X., Cooley, S., Verneris, M., Walcheck, B., Miller, J. 2013. NK cell CD16 surface expression and function is regulated by a disintegrin and metalloprotease-17 (ADAM17). Blood 121, 3599-3608.

Romee, R., Schneider, S. E., Leong, J. W., Chase, J. M., Keppel, C. R., Sullivan, R. P., Cooper, M. A., Fehniger, T. A. 2012. Cytokine activation induces human memory-like NK cells. Blood 120, 4751-4760.

Romee, R, Leong J. W, Fehniger, T. A, 2014, Utilizing Cytokines to Function-Enable Human NK Cells for the Immunotherapy of Cancer, Hindawi Publishing Corporation Scientificy Article ID 205796

Romee R, Rosario M, Berrien-Elliott M M, Wagner J A, Jewell B A', Schappe T, Leong J W, Abdel-Latif S, Schneider S E, Willey S, Neal C C, Yu L, Oh S T, Lee Y S, Mulder A, Claas F, Cooper M A, Fehniger T A, 2016, Cytokine-induced memory-like natural killer cells exhibit enhanced responses against myeloid leukemia Sci Transl Med. September 21; 8(357):357ra123.

Rothe, A., Sasse, S., Topp, M. S., Eichenauer, D. A., Hummel, H., Reiners, K. S., Dietlein, M., Kuhnert, G., Kessler, J., Buerkle, C., Ravic, M., Knackmuss, S., Marschner, J. P., Pogge von Strandmann, E., Borchmann, P., Engert, A. 2015. A phase 1 study of the bispecific anti-CD30/CD16A antibody construct AFM13 in patients with relapsed or refractory Hodgkin lymphoma. Blood 125, 4024-4031.

Schlums, H., Cichocki, F., Tesi, B., Theorell, J., Beziat, V., Holmes, T. D., Han, H., Chiang, S. C., Foley, B., Mattsson, K., Larsson, S., Schaffer, M., Malmberg, K. J., Ljunggren, H. G., Miller, J. S., Bryceson, Y. T. 2015. Cytomegalovirus infection drives adaptive epigenetic diversification of NK cells with altered signaling and effector function. Immunity 42, 443-456.

Schuster, I. S., Coudert, J. D., Andoniou, C. E., Degli-Esposti, M. A. 2016. "Natural Regulators": NK Cells as Modulators of T Cell Immunity. Front Immunol 7, 235.

Spiess, C. et al., Alternative molecular formats for bispecific antibodies. 2015, Mol. Immunol., 67(2):95-106

Spits, H., Artis, D., Colonna, M., Diefenbach, A., Di Santo, J. P., Eberl, G., Koyasu, S., Locksley, R. M., McKenzie, A. N., Mebius, R. E., Powrie, F., Vivier, E. 2013. Innate lymphoid cells—a proposal for uniform nomenclature. Nat Rev Immunol 13, 145-149.

Sun, J. C., Ugolini, S., Vivier, E. 2014. Immunological memory within the innate immune system. EMBO J 33, 1295-1303.

Tesi, B., Schlums, H., Cichocki, F., Bryceson, Y. T. 2016. Epigenetic Regulation of Adaptive NK Cell Diversification. Trends Immunol 37, 451-461.

Vivier, E., Morin, P., O'Brien, C., Druker, B., Schlossman, S. F., Anderson, P. 1991. Tyrosine phosphorylation of the Fc gamma RIII(CD16): zeta complex in human natural killer cells. Induction by antibody-dependent cytotoxicity but not by natural killing. J Immunol 146, 206-210.

Weichel et al., TandAbs: potent and well-manufacturable bi-specific antibodies; European Pharmaceutical Review 2015, vol. 20:27-32

Weinberg, R. A., The Biology of Cancer, 2013, $2^{nd}$ Edition, Taylor and Francis Wherry, E. J., Kurachi, M. 2015. Molecular and cellular insights into T cell exhaustion. Nat Rev Immunol 15, 486-499.

Wiernik, A., Foley, B., Zhang, B., Verneris, M. R., Warlick, E., Gleason, M. K., Ross, J. A., Luo, X., Weisdorf, D. J., Walcheck, B., Vallera, D. A., Miller, J. S. 2013. Targeting natural killer cells to acute myeloid leukemia in vitro with a CD16x33 bispecific killer cell engager and ADAM17 inhibition. Clin Cancer Res 19, 3844-3855.

Zompi, S., Colucci, F. 2005. Anatomy of a murder—signal transduction pathways leading to activation of natural killer cells. Immunol Lett 97, 31-39.

---

The invention claimed is:

1. A method of NK-cell based immunotherapy for treating cancer,
comprising administering to a subject in need thereof
(i) an antigen binding protein comprising at least one antigen binding site formed by a variable heavy chain domain and a variable light chain domain of an immunoglobulin for binding to CD16A to activate cytotoxicity of NK cells through CD16A engagement, and
(ii) at least one cytokine selected from the group consisting of interleukin 2 (IL-2), interleukin 12 (IL-12), interleukin 15 (IL-15), interleukin 18 (IL-18), and a combination thereof,
wherein the antigen binding protein is administered intermittently in intervals comprising an exposure free period to the antigen binding protein between two consecutive doses of the antigen binding protein, and wherein the intermittent administration comprises the steps of:
(a) administering a first dose of the antigen binding protein; and
(b) administering a second dose of the antigen binding protein after at least 3 times the half-life of the antigen binding protein subsequent to step (a), and
(c) administering a dose of at least one cytokine only during the interval from step (a) to step (b);
wherein steps (a), (b), and (c) are repeated at least 3 times.

2. The method of claim 1, wherein steps (a), (b), and (c) are repeated at least 5 times.

3. The method of claim 1, wherein the cytokine is administered after at least one half-life of the antigen binding protein subsequent to step (a).

4. The method of claim 1, wherein the antigen binding protein has a half-life of less than 1 week.

5. The method of claim 1, wherein the antigen binding protein comprises at least two antigen binding sites binding to CD16A.

6. The method of claim 5, wherein the antigen binding protein is multispecific and comprises at least one further antigen binding site binding to a tumor antigen.

7. The method of claim 1, wherein the at least one cytokine is interleukin 2 (IL-2) or interleukin 15 (IL-15).

8. The method of claim 6, wherein the antigen binding protein comprises at least two antigen binding sites binding to the tumor antigen.

9. The method of claim 8, wherein the antigen binding protein is a bispecific and tetravalent tandem diabody.

10. The method of claim 6, wherein the tumor antigen is selected from the group consisting of CD30, EGFR, EGFRvIII and BCMA.

11. The method 10 claim 10, wherein the antigen binding protein is a tandem diabody.

12. The method of claim 1, further comprising a preceding step of stimulating NK cells selected from the group consisting of in vivo stimulation and ex vivo stimulation by a cytokine.

13. The method of claim 12, which comprises a step of ex vivo stimulation of NK cells, wherein the NK cells are autologous or allogenic.

14. The method of claim 1, wherein the antigen binding protein is devoid of an immunoglobulin constant domain.

15. The method of claim 14, wherein the antigen binding protein is selected from the group consisting of Fab, Fab', F(ab')2, Fv fragments, single-chain Fv, tandem single-chain Fv ((scFv)$_2$), bi-specific Killer Engagers (BiKE), tri-specific Killer Engagers (TriKE), dual affinity retargeting antibodies (DARTTM), diabody (Db), single chain diabody (scDb) and tandem diabody, and tribody.

16. The method of claim 7, wherein interleukin 2 (IL-2) is administered in an amount of less than 6.0 million units/m$^2$/day.

17. The method of claim 4, wherein the antigen binding protein has a half-life of less than 72 hours.

18. The method of claim 17, wherein the antigen binding protein has a half-life of less than 24 hours.

19. The method of claim 18, wherein the second dose of the antigen binding protein is administered after at least 3 days subsequent to step (a).

20. The method of claim 6, wherein the antigen binding protein has a half-life of less than 72 hours.

21. The method of claim 20, wherein the antigen binding protein has a half-life of less than 24 hours.

22. The method of claim 21, wherein the second dose of the antigen binding protein is administered after at least 3 days subsequent to step (a).

23. The method of claim 6, wherein the at least one cytokine is interleukin 2 (IL-2) or interleukin 15 (IL-15).

24. The method of claim 23, wherein interleukin 2 (IL-2) is administered in an amount of less than 6.0 million units/m$^2$/day.

25. The method of claim 11, wherein the at least one cytokine is interleukin 2 (IL-2) or interleukin 15 (IL-15).

26. The method of claim 25, wherein interleukin 2 (IL-2) is administered in an amount of less than 6.0 million units/m2/day.

27. The method of claim 11, wherein the second dose of the antigen binding protein is administered after at least 3 days subsequent to step (a).

28. The method of claim 11, wherein the cytokine is administered 20-36 hours subsequent to step (a).

* * * * *